United States Patent
Kang et al.

(10) Patent No.: US 9,012,229 B2
(45) Date of Patent: Apr. 21, 2015

(54) CAPILLARY ELECTROPHORESIS METHOD FOR FINE STRUCTURAL ANALYSIS OF ENOXAPARIN SODIUM

(75) Inventors: Jingwu Kang, Shanghai (CN); Xueqiang Zhan, Shanghai (CN)

(73) Assignees: Hangzhou Jiuyuan Gene Engineering Co., Ltd., Zhejiang (CN); Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 13/982,100

(22) PCT Filed: Jan. 20, 2012

(86) PCT No.: PCT/CN2012/070677
§ 371 (c)(1),
(2), (4) Date: Jul. 26, 2013

(87) PCT Pub. No.: WO2012/100733
PCT Pub. Date: Aug. 2, 2012

(65) Prior Publication Data
US 2013/0309655 A1   Nov. 21, 2013

(30) Foreign Application Priority Data
Jan. 28, 2011 (CN) .......................... 2011 1 0027329

(51) Int. Cl.
| | |
|---|---|
| *G01N 33/00* | (2006.01) |
| *C12Q 1/34* | (2006.01) |
| *B01D 57/02* | (2006.01) |
| *G01N 27/26* | (2006.01) |
| *G01N 33/94* | (2006.01) |
| *G01N 27/447* | (2006.01) |
| *G01N 33/15* | (2006.01) |
| *C08B 37/00* | (2006.01) |
| *C07H 11/00* | (2006.01) |
| *C07H 13/04* | (2006.01) |

(52) U.S. Cl.
CPC ................ *G01N 27/26* (2013.01); *G01N 33/94* (2013.01); *G01N 2333/988* (2013.01); *G01N 2400/40* (2013.01); *G01N 27/447* (2013.01); *G01N 33/15* (2013.01); *C08B 37/0075* (2013.01); *C07H 11/00* (2013.01); *C07H 13/04* (2013.01); *C08B 37/0078* (2013.01)

(58) Field of Classification Search
USPC ................. 436/94; 435/18; 204/452
See application file for complete search history.

(56) References Cited

FOREIGN PATENT DOCUMENTS

WO   2009141821 A1   11/2009

OTHER PUBLICATIONS

Zhan, X. Fine Structure Analysis of Enoxaparin Sodium Base on Capillary Electrophoresis; Master's Thesis, Donhua University, Jan. 13, 2011. pp. i-57.*
Shafaati et al. Application of Capillary Zone Electrophoresis With Direct UV Detection to the Determination of a Model Drug, Vigabatrin, in Dosage Forms; Journal of Pharmacy and Pharmaceutical Science, vol. 8, No. 2 (2005) pp. 190-198.*
Kakehi et al. Analysis of Glycoproteins and the Oligosaccharides Thereof by High Performance Capillary Electrophoresis-Significance in Regulatory Studies on Biopharmaceutical Products; Biomedical Chromatography, vol. 16 (2002) pp. 103-115.*
Desai et al. Oligosaccharide Composition of Heparin and Low-Molecular-Weight Heparins by Capillary Electrophoresis; Analytical Biochemistry, vol. 213 (1993) pp. 120-127.*
An et al. Improved Capillary Electrophoretic Separation and Mass Spectrometric Detection of Oligosaccharides; Journal of Chromatography A, vol. 1004 (2003) pp. 121-129.*
Pervin et al. Separation of Glycosaminoglycan-Derived Oligosaccharides by Capillary Electrophoresis Using Reverse Polarity; Analytical Biochemistry, vol. 221 (1994) pp. 182-188.*
Zieske et al. Multi-Dimensional Mapping of Pyridylamine-Labeled N-Linked Oligosaccharides by Capillary Electrophoresis; Journal of Chromatography A, vol. 720 (1996) pp. 395-407.*
Oefner et al. Capillary Electrophoresis of Carbohydrates; Glycobiology, vol. 4, No. 4 (1994) pp. 397-412.*

* cited by examiner

*Primary Examiner* — Susan Hanley
*Assistant Examiner* — Paul Martin
(74) *Attorney, Agent, or Firm* — Morgan, Lewis & Bockius LLP

(57) ABSTRACT

A capillary electrophoresis method for quantitatively analyzing characteristic oligosaccharide present in enoxaparin sodium is provided in this invention. The method may be used for quantitatively determining the contents of disaccharides, trisaccharides, tetrasaccharides and in particular oligosaccharides having a 1,6-anhydro ring, which are unique compounds for enoxaparin sodium, within an exhaustively digested enoxaparin sodium sample with a mixture of heparinase I, II, and III, so as to quantitatively determine the molar percentage of oligosaccharides having 1,6-anhydro ring in enoxaparin sodium. The method may be used for the pharmaceutical quality control of enoxaparin sodium during the manufacturing process.

17 Claims, 3 Drawing Sheets

CAPILLARY ELECTROPHORESIS METHOD FOR FINE STRUCTURAL ANALYSIS OF ENOXAPARIN SODIUM

FIELD OF THE INVENTION

The invention relates to the field of analytical chemistry and pharmaceutical analysis, in detail, relates to a capillary electrophoresis (CE) method for quantitatively compositional analysis of enoxaparin sodium, that is to say, determining the building blocks of enoxaparin sodium, including disaccharides, trisaccharides, tetrasaccharides and oligosaccharides with 1,6-anhydro ring structure.

BACKGROUND OF THE INVENTION

Heparin is a highly sulfated, microheterogeneous and polydisperse polysaccharide comprising repeating disaccharide units composed of uronic acid (L-iduronic acid, IdoA or D-glucuronic acid, GlcA) and glucosamine (α-D-glucosamine, GlacN). It has good anticoagulant and antithrombotic activities and thereby is clinically used to prevent venous thrombosis after operation. Enoxaparin sodium represents a low molecular weight heparin, which is obtained by esterifying heparin extracted from intestinal mucosa in pigs to give benzyl ester derivatives of heparin sodium, and then derived from heparin by alkaline degradation. Compared to other heparins, enoxaparin sodium is more complicated in composition because of structural alterations (such as the difference in sulfation sites and numbers) induced by chemical manufacturing procedures. The weight-average molecular weight of enoxaparin sodium is ranging from 3,800 to 5,000 Da; wherein approximately 20% oligosaccharides have a molecular weight of less than 2,000 Da; more than 68% oligosaccharides have a molecular weight between 2,000 and 8,000 Da; and no more than 18% oligosaccharides have a molecular weight of higher than 8,000 Da.

During the manufacturing process, alkaline degradation undergoes two main competitive chemical reactions, namely, β-elimination and hydrolysis of benzyl ester. After degradation, a low molecular weight heparin is obtained in which oligosaccharide chain having an average molecular weight of about 4,500 (U.S. Pat. No. 5,389,618). The resulting oligosaccharide chains of enoxaparin sodium still bear the pentasaccharide structure which displays similar anticoagulant activity present in the parent heparin polysaccharide chains, and such a pentasaccharide sequence accounts for 15-25% in enoxaparin sodium.

During the process of restrictive degradation of heparin, desulfation and deamination may occur, and the glucosamine part at the reducing end of oligosaccharide may undergo the following characteristic conversions: (1) epimerization between glucosamine and mannosamine (T. Toida et al., J. Carbohydrate. Chem. 15(13), 351-360 (1996)), and (2) 6-O-desulfation of 6-O-sulfated glucosamine, to form a structure called 1,6-anhydro ring. These reactions enhance the structural complexity and diversity of enoxaparin sodium. Besides the above mentioned conversions, structural alterations also occur in sugar chain length, sequence and fine structure of building blocks.

The 1,6-anhydro structure at the reducing end of oligosaccharide is a characteristic structure of enoxaparin sodium. The ratio of 1,6-anhydro ring structure refers to the molar percentage of oligosaccharide chains with 1,6-anhydro ring structure. The ratio of 1,6-anhydro ring structure has been used as a criterion in pharmaceutical quality control of enoxaparin sodium as required by the United States Pharmacopoeia and European Pharmacopoeia. According to the European Pharmacopoeia, oligosaccharide chains with 1,6-anhydro ring structure should account for 15-25% of the total oligosaccharide chains.

However, the highly complex structure of enoxaparin sodium (such as the high non-uniformity and difference in the degree of sulfation of disaccharide unit) makes the analysis of its fine structure very difficult.

Strong anion exchange high performance liquid chromatography (SAX-HPLC) is the first choice in analyzing the sulfated oligosaccharide components of enoxaparin sodium. In addition, high performance liquid chromatography or low pressure gel permeation chromatography (GPC) is an effective tool for separating polysaccharide and desalting based on the molecular weight. Chromatographic methods for analysis of completely enzymatic digested samples of enoxaparin have been reported in many literatures (for example, CN03822562.X and CN200580009444.0). Nevertheless, when determined by strong anion exchange chromatography (SAX), several disaccharides cannot be baseline resolved, the α and β anomers at the reducing end of oligosaccharide must be eliminated by reduction with sodium borohydride to avoid the peak split.

Alternatively, capillary electrophoresis (CE) has been increasingly used to analyze sulfated polysaccharides (cf. U.S. Pat. No. 7,575,886 B2, Ampofo, S. et al., Anal. Biochem. 199:249-255 (1991); Malsch et al., J. Chromatogr. A. 716: 258-268 (1995)). However, the method for separating and determining the ratio of 1,6-anhyro ring structure formation by capillary electrophoresis has never been reported.

Matrix assisted laser desorption ionization/time of flight mass spectrometry (MALDI-TOF-MS), which does not require the steps of chromatography, can also be used for the analysis of heparin, and it has be used to sequence oligosaccharide chains (H. Sakaguchi et al., J. Biochem. 129 (2001) 107-118; A. J. Rhomberg, et al., Proc. Nalt. Acad. Sci. USA 95 (1998) 4176-4181; L. Sturiale, et al., Semin. Thromb. Hemost. 27 (2001) 465-472). However, MALDI-TOF-MS is not suitable for analyzing the sample with complex component such as the intact enoxaparin, and is not suitable used for controlling product quality owing to its high cost.

SUMMARY OF THE INVENTION

One object of the present invention is to provide a novel CE-based analysis method for quantitative compositional analysis of enoxaparin sodium. With this method all the building blocks of enoxaparin including disaccharides, trisaccharides, tetrasaccharides and four 1,6-anhydro oligosaccharides can be measured qualitatively and quantitatively.

Another object of the present invention is to provide a novel method for determining the molar percentage of oligosaccharide chain with 1,6-anhydro ring structure in enoxaparin sodium (generally called the ratio of 1,6-anhydro ring structure). The method can be used for quality control of enoxaparin sodium drug in the process of production. This method is completely different from the SAX-HPLC method used for determining the ratio of 1,6-anhydro ring structure.

The CE method involved in the invention can be used to separate and quantitatively determine disaccharides, trisaccharides, and tetrasaccharides obtained from the exhaustively enzymatic digested enoxaparin sodium, and particularly to determine the percentage of oligosaccharide chains with the 1,6-anhydro ring structure which is the characteristic structure of enoxaparin sodium.

The invention provides a method for fine structural analysis of enoxaparin sodium, comprising the following steps:

(1) digesting an enoxaparin sodium sample exhaustively with a mixture of heparin degrading enzymes;

(2) separating oligosaccharides in the digested enoxaparin sodium sample with capillary electrophoresis, wherein the oligosaccharides include disaccharides, triaccharides, tetrasaccharides and oligosaccharides with 1,6-anhydro structure;

(3) pairing peaks present in a electropherogram from the capillary electrophoresis to the oligosaccharides in the digested enoxaparin sodium sample according to the linear relationship between electrophoretic mobilities and charge-to-mass ratio of the oligosaccharides; and (4) quantitatively determining the percentage of each oligosaccharide in total oligosaccharides in the digested enoxaparin sodium sample by using a measured normalized chromatographic peak area.

The current CE method discloses digesting enoxaparin sodium sample exhaustively with mixed heparin degrading enzymes, and then separating and analyzing the depolymerized product by capillary electrophoresis. The mixed heparin degrading enzymes may include at least two of heparinase I (EC 4.2.2.7), heparinase II (without EC number) and heparinase III (EC 4.2.2.8), preferably including all three heparinases, and most preferably including all three heparinases mixed in a ratio of 1:1:1.

Four oligosaccharides with the 1,6-anhydro ring structure may be present in the completely depolymerized products of enoxaparin sodium:

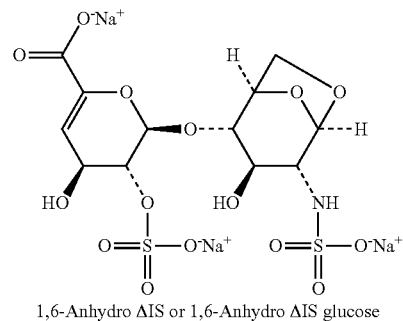

1,6-Anhydro ΔIS or 1,6-Anhydro ΔIS glucose

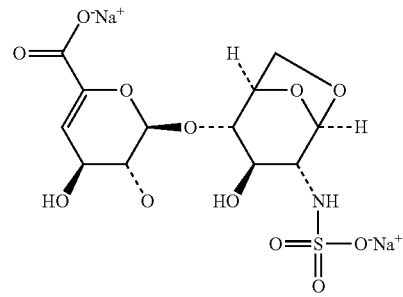

1,6-Anhydro ΔIIS or 1,6-Anhydro ΔIIS glucose

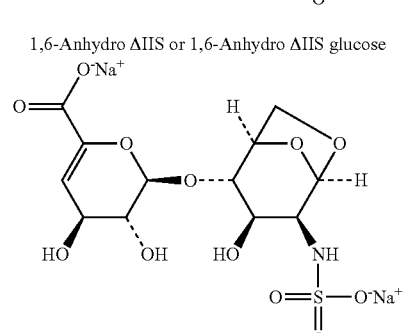

1,6-Anhydro ΔIIS epi or 1,6-Anhydro ΔIIS mannose

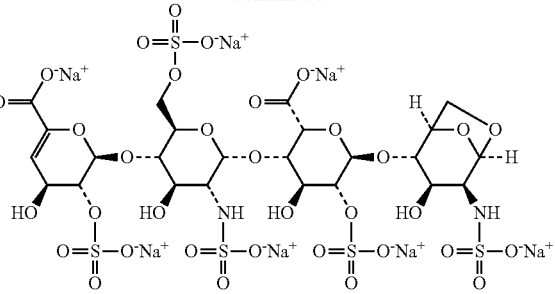

1,6-Anhydro ΔIS-IS epi or 1,6-Anhydro ΔIS-IS mannose

If there is no 2-O-sulfated group in uronic acid of the disaccharide adjacent to disaccharide unit terminated with 1,6-anhydro derivatives, 1,6-anhydro ring structure will exist as a disaccharides after exhaustively digested by heparinases; and when there is a 2-O-sulfated group in uronic acid of the disaccharide adjacent to disaccharide unit terminated with 1,6-anhydro ring, and the 1,6-anhydro ring structure exists in a manosamine, the oligosaccharide with 1,6-anhydro ring structure will exist as a tetrasaccharide (this form can prevent the tetrasaccharide from enzymatic digestion).

There may be a trisaccharide in the exhaustively digested samples. The trisaccharide 1, which is formed during other degradation process, has a structure as follows:

Trisaccharide 1

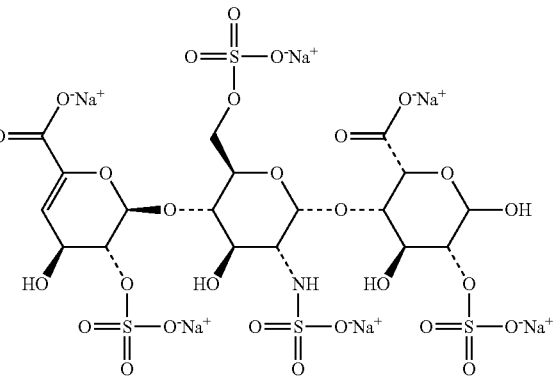

Other components in the exhaustively digested samples include 8 disaccharides (see below for ΔIS, ΔIIIS, ΔIIS, ΔIVS, ΔIA, ΔIIA, ΔIIIA, and ΔIVA). They do not have any characteristics of enoxaparin sodium and may have the following structures:

ΔIA

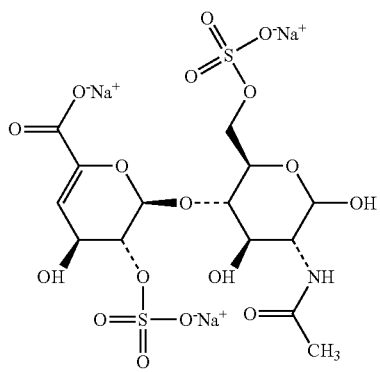

ΔIS

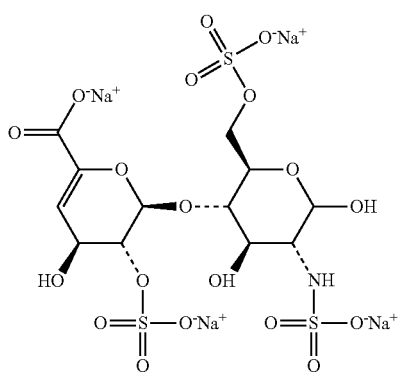

ΔIIA

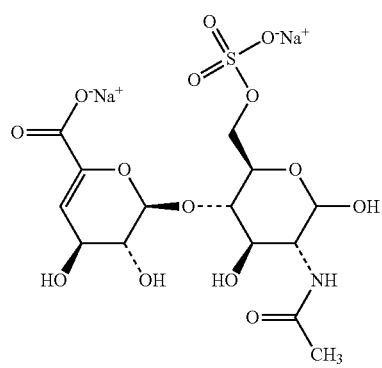

ΔIIS

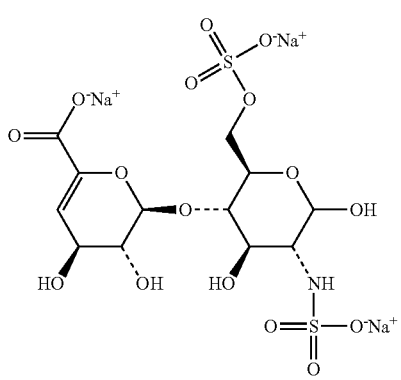

ΔIIIA

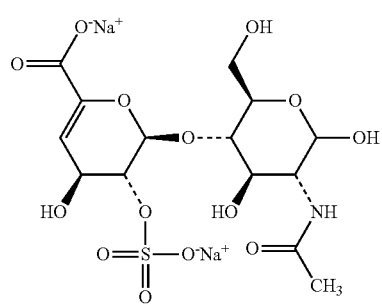

ΔIIIS

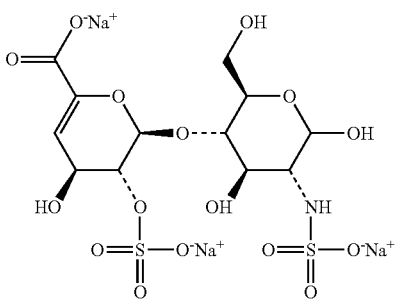

ΔIVA

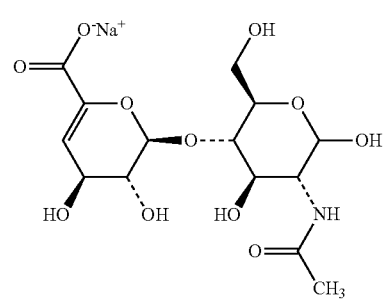

ΔIVS

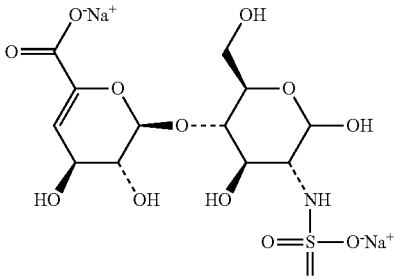

Moreover, two disaccharide ΔIIS$_{gal}$ and ΔIVS$_{gal}$, which contain a galacturonic acid produced by 2-O-desulfation of -IdoA(2S)-GlacNS(6S) and -IdoA(2S)-GlacNS, probably could be detected in the exhaustively digested samples by the current method. The two disaccharides generally do not exist in the original structure of heparin (U. M. Desai et al., Arch. Biochem. Biophys. 306(2)461-468 (1993)).

ΔIISgal

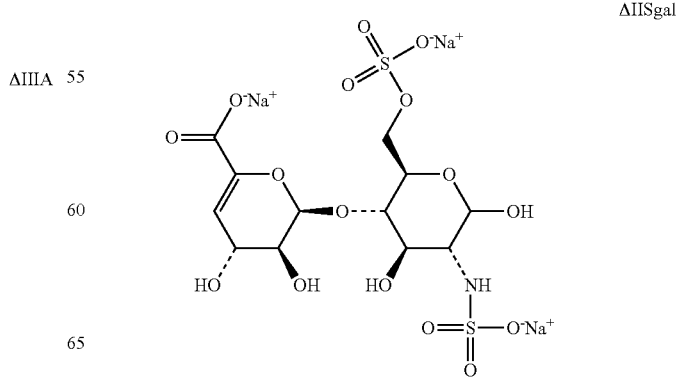

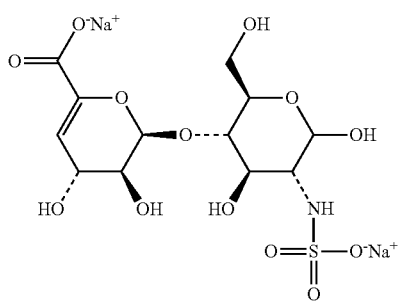
ΔIVSgal

Two tetrasaccharides present in most low molecular weight heparins (LMWHs) are shown as follows. They may be resistant from the enzymatic digestion, and they may reflect fragments which have affinity to antithrombin III. The two tetrasaccharides are represented by the following symbols: ΔIIA-IISglu and ΔIIa-IVSglu (S. Yamada, et al., J. Biol. Chem.; 270(7), 4780-4787 (1993)).

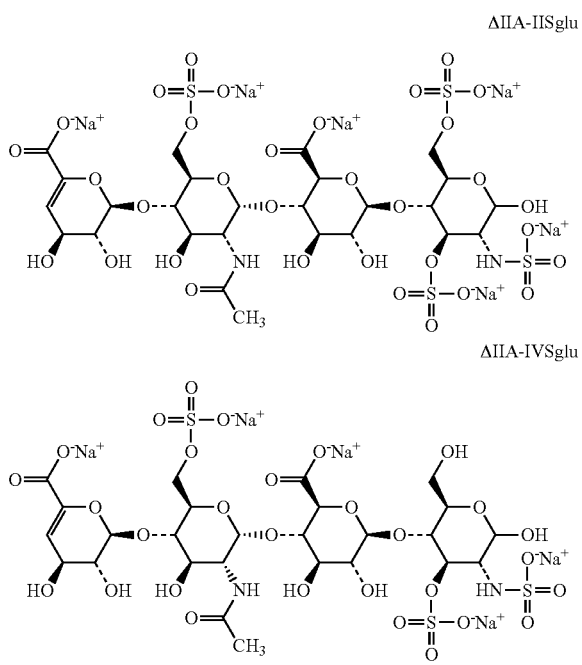

ΔIIA-IISglu

ΔIIA-IVSglu

The structural identification of the above mentioned disaccharides, trisaccharides, tetrasaccharides and oligosaccharides with 1,6-anhydro ring structure may also be found in United States Pharmacopoeia (Second Supplement, USP-NF, Chemical Tests/<207>1,6-Anhydro Derivative for Enoxaparin sodium).

The invention provides a CE method for separating disaccharide, trisaccharide, tetrasaccharide, and oligosaccharide with 1,6-anhydro ring structure in an exhaustively digested enoxaparin sodium sample.

The CE may use a fused silica capillary, a running buffer, a separation voltage, an injection pressure, an injection time, a capillary temperature; and a UV detection wavelength.

The fused silica capillary used in the invented method may have a total length in the range from 50 to 100 cm, and an inner diameter ranging from 25 to 75 μm. The effective length of the capillary is usually the length from the inlet end to the detection window and may be calculated by subtracting 10 cm from the total length, and may vary slightly depending on the type of capillary electrophoresis instrument.

In another embodiment of the invention, the fused silica capillary may have a total length ranging from 70 to 100 cm, and an inner diameter ranging from 40 to 60 μm.

The running buffer for capillary electrophoresis may be selected from $NaH_2PO_4$—$H_3PO_4$, Tris-$H_3PO_4$ or $LiH_2PO_4$—$H_3PO_4$, in a concentration ranging from 150 to 300 mM, and in a pH ranging from 1.5 to 4.0.

In another embodiment of the invention, the preferred running buffer is selected from $NaH_2PO_4$—$H_3PO_4$, Tris-$H_3PO_4$ or $LiH_2PO_4$—$H_3PO_4$, in a concentration ranging from 200 to 250 mM, and in the pH ranging from 2.0 to 4.0.

In another embodiment of the invention, $MgCl_2$ or $ZnCl_2$ in a concentration ranging from 1 to 5 mM and polyethylene glycol (PEG) having a molecular weight from 5000 to 100000 in a concentration ranging from 0.1% to 5% (m/v) may be added to the above described running buffer. The aim of adding 0.1%~5% $MgCl_2$ or $ZnCl_2$ and PEG in the buffer solution is to modify the electrophoretic mobility of the oligosaccharides which may have close electrophoretic migration times, e.g. the electrophoretic migration times of ΔIS, trisaccharide and 1,6-anhydroΔIS-IS, and thereby improve the resolution of their separation.

In another embodiment of the invention, $MgCl_2$ or $ZnCl_2$ in a concentration ranging from 2 to 4 mM, and PEG (having a molecular weight from 10000 to 50000) in a concentration ranging from 1% to 3% (m/v) are preferably added to the above described running buffer.

The separation voltage applied on the capillary may be in the range from −15 to kV, preferably from −20 kV to −25 kV, which may vary depending on the type of capillary electrophoresis instrument.

The capillary electrophoresis method described in the invention may employ hydrodynamic injection. The injection pressure may be in the range from 1 to 100 mbar, and the injection time may be in the range from 1 to 60 s; preferably, the injection pressure may be in the range of from 30 to 60 mbar, and the injection time may be in the range of from 5 to 30 s; more preferably, the injection pressure may be in the range of from 40 to 50 mbar, and the injection time may be in the range of from 10 to 20 s.

During the electrophoresis process, after the last sulfated disaccharide ΔIIA pass through the detection window, an alternative pressure may be applied to push ΔIVA passing through the detection window for detection. The pressure may be in the range of from 5 to 150 mbar, preferably from 5 to 30 mbar, from 10 to 20 mbar or from 30 to 150 mbar depending on the type of capillary electrophoresis instruments.

The capillary temperature used in the invention may be in the range from 10 to 40° C., preferably from 20 to 30° C.

The UV detection wavelength used in the invention may be in the range from 230 to 235 nm; preferably from 230 to 232 nm.

Overall, the separation conditions of capillary electrophoresis may be optimized as follows: the fused silica capillary may have a total length ranging from 50 to 100 cm and have an inner diameter ranging from 25 to 75 μm; the running buffer may be selected from $NaH_2PO_4$—$H_3PO_4$, Tris-$H_3PO_4$ or $LiH_2PO_4$—$H_3PO_4$ in a concentration ranging from 150-300 mM and in a pH ranging from 1.5-4.0; The running buffer may contain $MgCl_2$ or $ZnCl_2$ in a concentration ranging from 1-5 mM, and PEG having a molecular weight ranging from 5000 to 100000 in a concentration ranging from 0.1%-5.0% (m/v) may be added to the running buffer before use; The applied voltage may be in the range from −15 to −30 kV. The pressure for hydrodynamic injection may be in the range from 1 to 100 mbar, and the injection time may be in the range from 1 to 60 s. After the last monosulfated disaccharide ΔIIA passing through the detection window, a pressure of 5-150 mbar may be applied to push ΔIVA passing through the detection window for detection. In the process of electrophoresis, the capillary may be thermostatted at 10-40° C., and the UV detection wavelength may be in the range from 230 to 235 nm.

In another embodiment of the invention the separation conditions of capillary electrophoresis may be optimized as follows: the fused silica capillary may have a total length ranging from 50 to 100 cm and an inner diameter ranging from 25 to 75 μm; the running buffer may include $NaH_2PO_4$—$H_3PO_4$, Tris-$H_3PO_4$ or $LiH_2PO_4$—$H_3PO_4$ at the concentration of 150-300 mM, and $MgCl_2$ or $ZnCl_2$ in a concentration ranging from 1-5 mM, in a pH ranging from 1.5-4.0; PEG having a molecular weight ranging from 5000 to 100000 in a concentration ranging from 0.1%-5.0% (m/v) may be added to the running buffer before use; the voltage applied on capillary may be in the range from −15 to −30 kV; for the hydrodynamic injection, the pressure may be in the range from 30 to 60 mbar, and the injection time may be in the range from 5 to 30 s; after the last monosulfated disaccharide ΔIIA passing through the detection window, a pressure of 5-150 mbar may be applied to pass ΔIVA through the detection window for detection; and in the process of electrophoresis, the capillary may be thermostatted at 10-40° C., and the UV detection wavelength may be in the range from 230 to 235 nm.

In another embodiment of the invention, optimized separation conditions of capillary electrophoresis are depicted as follows: the fused silica capillary may have a total length ranging from 70 to 100 cm and an inner diameter ranging from 40 to 60 μm; the running buffer may include $NaH_2PO_4$—$H_3PO_4$, Tris-$H_3PO_4$ or $LiH_2PO_4$—$H_3PO_4$ at the concentration of 200-250 mM, and $MgCl_2$ or $ZnCl_2$ in a concentration ranging from 2-4 mM, at a pH ranging from 2-4; PEG having a molecular weight ranging from 10000 to 50000 in a concentration ranging from 1%-3% (m/v) may be added to the running buffer before use; the voltage applied on the capillary may be in the range from −15 to −25 kV; for hydrodynamic injection, the pressure may be in the range from 40 to 50 mbar, and the injection time may be in the range from 10 to 20 s; after the last monosulfated disaccharide ΔIIA passing through the detection window, a pressure of 10-20 mbar may be applied to pass ΔIVA through the detection window for detection; and in the process of electrophoresis, the capillary may be thermostatted at 20-30° C.; and the UV detection wavelength may be in the range from 230 to 232 nm.

In another preferred embodiment, the invention provides an optimized separation condition of capillary electrophoresis:

the capillary may an inner diameter of 50 μm and a total length of 85 cm; the buffer solution may include Tris-$H_3PO_4$ of 200 mM and $MgCl_2$ of 2 mM, at pH 2.5; polyethylene glycol of 1% (m/v) having a molecular weight of 10000 may be added to the running buffer before use; the injection pressure may be 50 mbar, and the injection time may be 15 s; the separation voltage may be −25 kV; after the monosulfated disaccharide ΔIIA passing the detection window, 20 mbar of pressure may be applied to push ΔIVA to the detection window for detection; the column temperature may be 25° C.; and the UV detection wavelength may be 232 nm.

In another preferred embodiment, the invention provides another optimized separation condition of capillary electrophoresis:

the capillary may have an inner diameter of 50 μm and a total length of 80 cm; the buffer solution may include Tris-$H_3PO_4$ of 200 mM and $MgCl_2$ of 2 mM, at pH 2.7; polyethylene glycol of 1.3% (m/v) having a molecular weight of 10000 may be added to the running buffer; the injection pressure may be 55 mbar, and the injection time may be 10 s; the separation voltage may be −22 kV; after the last monosulfated disaccharide ΔIIA passing through the detection window, 138 mbar of pressure may be applied to push ΔIVA to the detection window for detection; the column temperature may be 25° C.; and the UV detection wavelength may be 230 nm.

In another preferred embodiment, an electropherogram of exhaustively digested sample of heparin sodium may be shown in FIG. 3A; an electropherogram of exhaustively digested samples of enoxaparin sodium may be shown in FIG. 3B; and the experiments were performed on Agilent CE system.

In another preferred embodiment, an electropherogram of exhaustively digested sample of enoxaparin sodium may be shown in FIG. 4; and the experiment was performed on BECKMAN MDQ CE system.

The method of the invention may identify disaccharides present in the exhaustively digested sample of enoxaparin sodium using 7 standard samples of disaccharides (ΔIVA, ΔIS, ΔIIIS, ΔIIS, ΔIA, ΔIIA, ΔIIIA) For those oligosaccharides without standard samples available, electrophoretic mobility may be used as a qualitative index. The electrophoretic mobility may be the physiochemical parameter of the analytes. With a certain running buffer at a given temperature and at a given pH value, an analyte has a constant electrophoretic mobility (μ). Thus, electrophoretic mobility may be used to identify the corresponding peak in electropherogram. Electrophoretic mobility of each component can be calculated according to the equation 1

$$\mu = \frac{L_T \cdot L_D}{t \cdot V} \quad (1)$$

where $L_T$ and $L_D$ are the total length and effective length of a capillary, respectively; V is the applied voltage; and t is the migration time.

According to equation 2, electrophoretic mobility of a given analyte is linearly correlated with its charge-to-mass ratio.

$$\mu = \frac{Z}{6\pi \cdot \eta \cdot r} \quad (2)$$

where Z is effective charge of an ion, η is viscosity of the solution, and r is diameter of an ion.

The structures of all 17 oligosaccharides in the exhaustively digested sample of enoxaparin sodium are as illustrated above. Standard samples of at least 5 oligosaccharides may be subjected to electrophoresis to determine their electrophoretic mobility (μ). Subsequently, a correlation plot of electrophoretic mobility versus their charge-to-mass ratios may be constructed. Linear regression analysis may provide an equation to describe the relationship between electrophoretic mobility μ and charge-to-mass ratio Z/M. The electrophoretic mobility of other oligosaccharides can be deduced according to the linear equation, which can be used to identify these oligosaccharides in the absence of reference standards.

According to the invention, standard samples of six sulfated disaccharide, i.e. ΔIS, ΔIIIS, ΔIIS, ΔIA, ΔIIA, ΔIIIA, may be subjected to electrophoresis to determine their electrophoretic mobility (μ); then a correlation plot of electrophoretic mobility to their charge-to-mass ratio may be constructed; a linear equation of relationship between electrophoretic mobility μ and charge-to-mass ratio Z/M may be obtained by linear regression analysis; the electrophoretic mobility of other oligosaccharides may be predicted according to the linear equation which can be used to identify these oligosaccharides in the absence of reference standards.

In a preferred embodiment, electrophoretic mobility of 6 standards sulfated disaccharide samples may be determined, and then a correlation plot of electrophoretic mobility versus charge-to-mass ratios of corresponding disaccharides may be constructed as shown in FIG. 1 (at pH 2.5, only sulfo groups are charged, and thus the net charge of each oligosaccharide is approximately equivalent to the number of sulfo groups). The linear equation ($R^2=0.9995$) is given below:

$$\frac{Z}{M} = 1.56\mu - 0.30 \qquad (3)$$

where Z/M is charge-to-mass ratio of a oligosaccharide; and μ is the corresponding electrophoretic mobility of the given oligosaccharide.

The corresponding electrophoretic mobility (theoretical value is calculated according to equation 3) is listed in Table 1. In addition, table 1 gives other physiochemical parameters of oligosaccharide in exhaustively digesting enoxaparin sodium, including molecular weight, the number of $SO_3^-$ per saccharide unit, charge-mass ratio and measured electrophoretic mobility. The correlation plot of measured electrophoretic mobility versus theoretical electrophoretic mobility of individual oligosaccharide may be constructed as shown in FIG. 2. The measured value and theoretical value of electrophoretic mobility of individual oligosaccharide may be both generally distributed on the line of y=x, and provide a good correlation (0.98). Therefore, the invention may assign all peaks in an electropherogram from CE of the exhaustively digested enoxaparin sodium according to the linear relationship between electrophoretic mobility and charge-to-mass ratio.

The current invention may use seven standard disaccharide samples to identify the disaccharides present in the exhaustively digested enoxaparin sodium sample. As shown in FIG. 3, peaks 1-7 are peaks of sulfated disaccharides migrating in the migration order of ΔIS, ΔIIIS, ΔIIS, ΔIA, ΔIVS, ΔIIIA, ΔIIA Because the pH value (2.5) of running buffer is lower than the ionization constant (pKa) of carboxylic groups, non-sulfated disaccharide ΔIVA bearing a carboxylic group is difficult to ionize, and cannot be electrophoretically driven during the electrophoretic process, an alternative pressure must be applied to push ΔIVA to the detection window (peak 8 in FIG. 3).

In the present invention, owing to the linear relationship between electrophoretic mobility and charge-to-mass ratio, peak 9 is assigned as disaccharide $\Delta IIS_{gal}$, and peak 10 is identified as disaccharide galactose ΔIVSgal. The content of ΔIVSgal is very low, it cannot be observed in the electropherogram when pressure is applied in the process of the electrophoresis due to the broadening of adjacent peaks. Under the condition without pressure, peak 10 can be observed clearly as ΔIVSgal.

TABLE 1

Physiochemical parameters of oligosaccharides obtained from exhaustively digested enoxaparin sodium

| | | | The number of $SO_3^-$ per | Charge-to- | Electrophoretic mobility ($10^{-4}$) | |
|---|---|---|---|---|---|---|
| Peak No. | Oligosaccharide | Molecular weight | saccharide unit | mass ratio ($10^{-3}$) | Theoretical value | Measured value |
| 1 | ΔIS | 665 | 3 | 4.51 | 3.102 | 2.941 |
| 2 | ΔIIIS | 563 | 2 | 3.55 | 2.475 | 2.367 |
| 3 | ΔIIS | 563 | 2 | 3.55 | 2.475 | 2.314 |
| 4 | ΔIA | 605 | 2 | 3.31 | 2.318 | 2.231 |
| 5 | ΔIVS | 461 | 1 | 2.17 | 1.574 | 1.481 |
| 6 | ΔIIIA | 503 | 1 | 1.99 | 1.456 | 1.454 |
| 7 | ΔIIA | 503 | 1 | 1.99 | 1.456 | 1.423 |
| 8 | ΔIVA | 401 | 0 | 0 | 0.156 | — |
| 9 | $\Delta IIS_{gal}$ | 563 | 2 | 3.55 | 2.475 | 2.277 |
| 10 | $\Delta IVS_{gal}$ | 461 | 1 | 2.17 | 1.574 | — |
| 11 | ΔIIA-IISglu | 1168 | 2 | 3.48 | 2.429 | 2.432 |
| 12 | ΔIIA-IVSglu | 1066 | 1.5 | 2.81 | 1.991 | 2.057 |
| 13 | Trisaccharide | 965 | 2.67 | 4.15 | 2.867 | 2.923 |
| 14 | 1,6-AnhydroΔIS-IS | 1210 | 2.5 | 4.13 | 2.854 | 2.903 |
| 15 | 1,6-Anhydro ΔIS | 545 | 2 | 3.67 | 2.553 | 2.612 |
| 16 + 17 | 1,6-Anhydro ΔIIS | 443 | 1 | 2.26 | 1.632 | 1.693 |

Note:
The number of $SO_3^-$ per saccharide unit equals to the average number of $SO_3^-$ group carried by each disaccharide unit in oligosaccharide, and is calculated by dividing the total number of $SO_3^-$ groups by the number of saccharide units in an oligosaccharide (a saccharide unit represents a disaccharide unit consisting of a D-β-glucuronic acid (or L-α-iduronic acid) and a N-acetyl glucosamine).

In the present invention, peaks 11 and 12 (FIG. 3) are assigned as tetrasaccharide peaks according to the linear relationship between electrophoretic mobility and charge-to-mass ratio. Peak 11 is assigned as tetrasaccharide ΔIIA-IIS-glu, and peak 12 is assigned as tetrasaccharide ΔIIA-IVSglu.

In the present invention, when the sample is separated merely with basic buffer, peak 13 may be co-eluted with disaccharide IS (peak 1), and peak 14 may also partially merge with peak 1. A certain amount of PEG may be added to the buffer, rendering good resolution between peaks 1 and 13. This is because PEG may alter the peak time oligosaccharides based on their molecular weight, significantly improving the separation results.

In the present invention, a certain amount of $MgCl_2$ or $ZnCl_2$ may also be added to the running buffer to further improve the separation. $Mg^{2+}$ or $Zn^{2+}$ may modify the electrophoretic mobility of oligosaccharides by forming transient ion pairs with $SO_3^-$ groups attached in the oligosaccharide chains.

A trisaccharide may be produced by exhaustive enzymatic degradation of enoxaparin sodium. According to Equation 3, the linear equation of electrophoretic mobility and charge-to-mass ratio, peak 13 can be assigned as the trisaccharide.

Likewise, according to Equation 3, four 1,6-anhydro oligosaccharides can be identified. The charge-to-mass ratio of 1,6-anhydroΔIS-IS may be slightly less than that of trisaccharide (by 0.02). Thus, the peak near peak 13 (trisaccharide) may be assigned as 1,6-AnhydroΔIS-IS (peak 14). Moreover, the peak area ratio between 1,6-anhydroΔIS-IS and trisaccharide obtained by separating the exhaustively digested samples of enoxaparin sodium with SAX-HPLC can also be used for assignment of peaks corresponding to 1,6-anhydroΔIS-IS and trisaccharide in the electropherogram. The 1,6-anhydro ΔIS has a charge-to-mass ratio of 3.67, and thus peak 15 in electropherogram can be assigned as 1,6-anhydro ΔIS 1,6-Anhydro ΔIIS presents in the form of anomers, 1,6-anhydro-ΔIIS and 1,6-anhydroΔIIS epi, therefore they should have the same peak areas and migration times. Therefore, peaks 16 and 17 shown in FIG. 3 are assigned as 1,6-anhydro ΔIIS, and 1,6-anhydroΔIIS epi, respectively. Their normalized peak areas agree well with that obtained by separation with SAX-HPLC.

Each peak present in electropherogram of FIG. 3 is listed in Table 1.

Because the peak area of each component in electropherogram is proportional to its molar concentration, qualitative determination of each component can be achieved by using the normalized peak area, according to the following formula:

$$W_n \% = 100 \times \frac{Mw_n \times Area_n}{\sum Mw_x \times Area_x}$$

where, $Mw_n$ is the molecular weight of a given component, $Area_n$ is the peak area of this component, and $Mw_x$ and $Area_x$ are molecular weight and the peak area of a peak x corresponding to its number listed in Table 1, respectively.

According to an embodiment, the invention provides a method for determining the weight percentage of oligosaccharides with characteristic 1,6-anhydro ring structure in enoxaparin sodium, comprising the following steps:

(1) digesting an enoxaparin sodium sample exhaustively with a mixture of heparin degrading enzymes;

(2) separating oligosaccharides in the digested enoxaparin sodium sample by capillary electrophoresis, where in the oligosaccharides include disaccharides, triaccharides, tetrasaccharides and oligosaccharides with 1,6-anhydro structure;

(3) pairing peaks present in the electrophoregram from the capillary electrophoresis to the oligosaccharides in the digested enoxaparin sodium sample according to the linear relationship between electrophoretic mobility and charge-to-mass ratio of the oligosaccharides and identifying the peaks of the oligosaccharide with 1,6-anhydro ring structure; and (4) quantitatively determining the amount of the oligosaccharides with 1,6-anhydro ring structure according to their peak areas, and further determining the molar percentage of the 1,6-anhydro ring structure in the enoxaparin sodium.

In these steps, each parameter is the same as described above.

In the method of the invention, a widely accepted hypothesis is adopted: when all unsaturated oligosaccharides in exhaustively digested samples are detected at UV wavelength of 230~235 nm, they have the same absorbance, i.e., 5500 $mol^{-1} \cdot L^{-1} \cdot cm^{-1}$.

Therefore, the weight percentage of all components in exhaustively digested samples of enoxaparin sodium can be determined by using normalized peak area method. For example, the 1,6-anhydro disaccharide 1 (i.e. 1,6-anhydro ΔIIS), disaccharide 2 (i.e. 1,6-anhydro ΔIIS), disaccharide 3 (i.e. 1,6-anhydro ΔIS), and tetrasaccharide 1 (i.e. 1,6-anhydro ΔIS-IS) correspond to peaks 16, 17, 15, and 14, respectively, and their weight percentage can be calculated by the equations:

$$w_{16+17} \% = 100 \times \frac{433(Area_{16} + Area_{17})}{\sum (Mw_x \times Area_x)} \quad (4)$$

$$w_{14} \% = 100 \times \frac{545 \times Area_{14}}{\sum (Mw_x \times Area_x)} \quad (5)$$

$$w_{15} \% = 100 \times \frac{1210 \times Area_{15}}{\sum (Mw_x \times Area_x)}. \quad (6)$$

where $Area_{14}$, $Area_{15}$, $Area_{16}$, and $Area_{17}$ correspond to peak areas of peaks 14, 15, 16, and 17, respectively; The molecular weights of the four compounds are 545, 1210, 443, and 443, respectively; $Mw_x$ and $Area_x$ represents molecular weight and the peak area of each component in electropherogram, respectively If the weight-average molecular weight of enoxaparin sodium is $W_x$, the molar percentage of oligosaccharide chains with 1,6-anhydro ring structure in enoxaparin sodium can be calculated by formula (7) or (8):

$$1,6 Anhydro \% = Wx \times \left( \frac{w_{16+17} \%}{443} + \frac{w_{14} \%}{545} + \frac{w_{15} \%}{1210} \right) \quad (7)$$

$$1,6 Anhydro \% = 100 \times Wx \times \frac{(Area_{14} + Area_{15} + Area_{16} + Area_{17})}{\sum (Mw_x \times Area_x)} \quad (8)$$

The molar percentage of other components in enoxaparin sodium structure also can be calculated by the same method.

The method provided in the invention can be applied to fine structure identification or quantitative analysis of various polysaccharides, including heparin, low molecular weight heparin and ultra low molecular weight heparin.

BRIEF DESCRIPTION OF THE DRAWINGS

FIG. 3A is an electropherogram of exhaustively digested heparin sodium; FIG. 3B is the electropherogram of exhaustively digested enoxaparin sodium (USP reference standard). The experiments are performed on Agilent CE system.

DETAILED DESCRIPTIONS

Example 1

Sample Preparation (1) Preparation of sodium acetate/calcium acetate solution at pH 7.0:10 mg of bovine serum albumin and 32 mg of acetate calcium were dissolved in 60 mL water, and then 580 μL of glacial acetic acid was added. After being adjusted to pH 7.0 by using 2 M of NaOH solution, the solution was transferred to 100 mL volumetric flask, and diluted with water to the final volume of 100 mL. The resulting solution was filtered through a 0.45 μm membrane filter prior to use.

(2) Preparation of potassium phosphate buffer at pH 7.0:68 mg of potassium dihydrogen phosphate and 10 mg of bovine serum albumin were dissolved in 30 mL water and adjusted to pH 7.0 with potassium hydroxide solution. The solution was transferred to 50 mL volumetric flask, and diluted with water to the final volume of 50 mL.

(3) Preparation of heparinase solution: each heparinase (I, II and III) was individually dissolved with potassium phosphate buffer solution (pH 7.0) to give a solution at concentration of 0.4 IU/mL. The solution was stored at −20° C. until ready to use.

(4) Preparation of a mixture of heparinase I, heparinase II and heparinase III: The three heparinase solutions were mixed in a ratio of 1:1:1.

(5) Preparation of enoxaparin sodium solution: 20 mg of enoxaparin sodium was dissolved in 1 mL water to produce a 20 mg/mL solution.

(6) Exhaustively digesting enoxaparin sodium sample: 20 μL of enoxaparin sodium solution, 70 μL of sodium acetate/calcium acetate solution (pH 7.0), and 100 μL of heparinases (I, II, III) mixture were gently mixed, and then the mixture was incubated in 25° C. water bath for 48 h. Subsequently, the digested mixture was injected in CE to perform electrophoresis.

(7) Exhaustively digesting heparin sodium sample: 20 μL of heparin sodium solution, 70 μL of sodium acetate/calcium acetate solution (pH 7.0), and 100 μL of heparinases (I, II, III) mixture were gently mixed, and then the mixture was incubated in 25° C. water bath for 48 h. Subsequently, the digested sample was injected in CE to perform electrophoresis.

Figure 1:
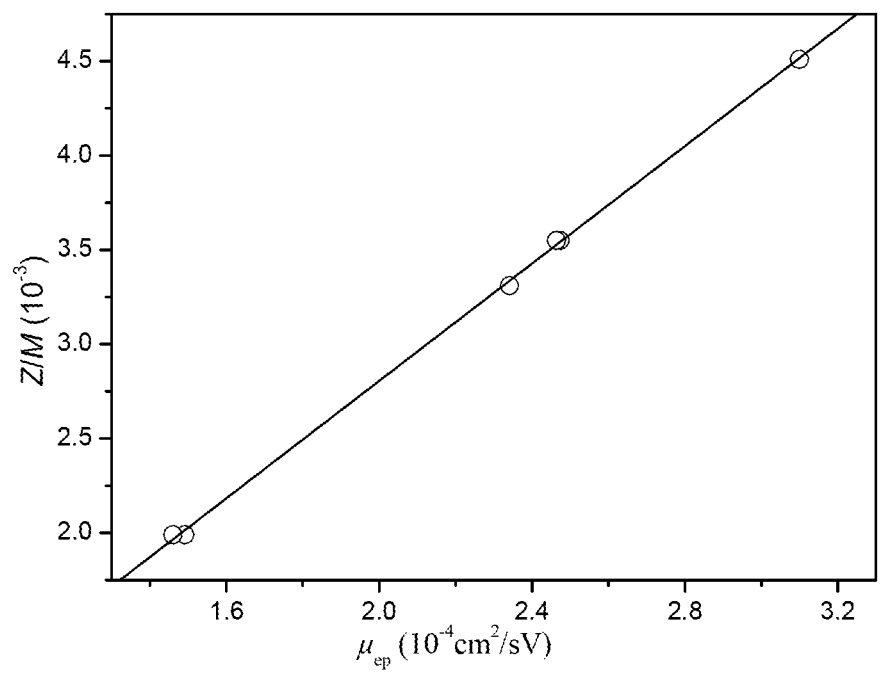
FIG. 1 shows the correlation plot of electrophoretic mobility versus charge-mass ratio of standards samples for six sulfated disaccharides.

(8) 20 μL of each of 7 disaccharide reference standards (ΔIVA, ΔIS, ΔIIIS, ΔIIS, ΔIA, ΔIIA, ΔIIIA) solution was mixed. The resulting mixture was separated under the CE conditions as described in Example 2. Electrophoretic mobility of 6 sulfated disaccharide standards was determined The correlation plot (FIG. 1) of the electrophoretic mobility versus charge-to-mass ratio of disaccharides was constructed and give a linear equation ($R^2=0.9995$):

$$\frac{Z}{M} = 1.56\mu - 0.30$$

where Z/M is charge-to-mass ratio of an oligosaccharide; and n is the corresponding electrophoretic mobility of the given oligosaccharide.

Figure 2:
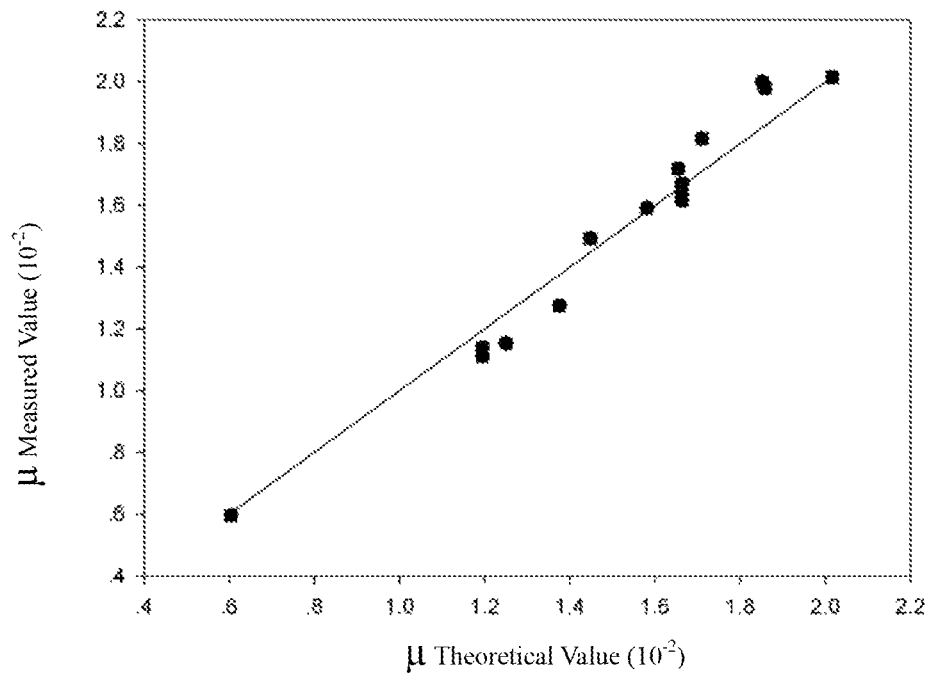
FIG. 2 shows the correlation plot of measured value versus theoretical value of electrophoretic mobility of oligosaccharides.

(9) The correlation plot of measured value and theoretical value of electrophoretic mobility of each oligosaccharide was shown in FIG. 2. The measured and theoretical value of electrophoretic mobility of each oligosaccharide were both generally distributed on the line of y=x, and give a good correlation coefficient of 0.98.

Example 2

Conditions of Capillary Electrophoresis

Separations by CE were performed on Agilent CE system. The fused silica capillary had an inner diameter of 50 μm, an outer diameter of 370 μm, a total length of 85 cm, and an effective length of 75 cm; the running buffer solution consisted of 200 mM Tris-$H_3PO_4$ and 2 mM $MgCl_2$, at pH 2.5; 1% (m/v) polyethylene glycol with molecular weight of 10000 should be added to the buffer solution immediately before use; the injection pressure was 50 mbar, and the injection time was 15 s; the separation voltage was −25 kV; after the monosulfated disaccharide ΔIIA was eluted (about 34 min), a pressure of 20 mbar was applied to push ΔIVA to the detection window for detection; the column temperature was 25° C.; and the UV detection wavelength was 232 nm.

The electropherogram of exhaustively digested enoxaparin sodium and heparin sodium by capillary electrophoresis were shown in FIG. 3A and FIG. 3B, respectively.

Example 3

Sample Analysis 1

Figure 3:
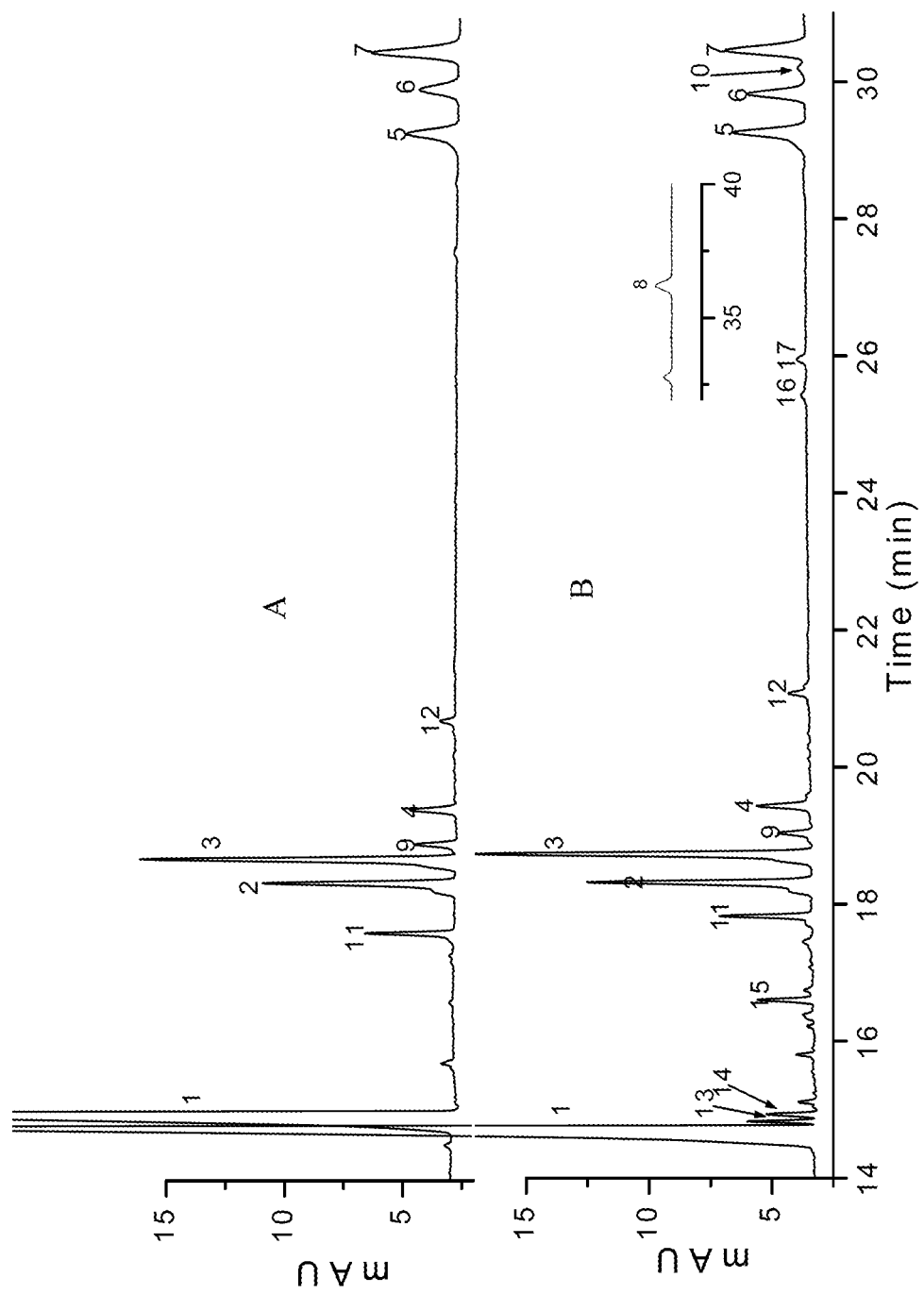
FIG. 3 illustrates the electrophoretic separation of exhaustively digested samples of enoxaparin sodium and heparin sodium by CE, where

As shown in FIG. 3, only the products of exhaustive digested enoxaparin sodium contained 1,6-anhydro oligosaccharides. According to the formula $$W_n \% = 100 \times \frac{Mw_n \times Area_n}{\sum Mw_x \times Area_x},$$

or formulae (4), (5) and (6), the weight percentage of each oligosaccharide obtained from exhaustively digested enoxaparin sodium was calculated (as listed in Table 2), in which 1,6-anhydro oligosaccharides 14, 15 and 16+17 account for 1.61%, 0.95% and 0.64%, respectively. It was known that the USP enoxaparin sodium tested in our experiment had a weight-average molecular weight of 4432. The molar percentage of oligosaccharide chains with 1,6-anhydro ring structure in enoxaparin sodium was 19.99%, calculated by formula (7) or (8).

TABLE 2

The weight percentage of each oligosaccharide obtained from exhaustively digested enoxaparin sodium:

| Peak number | Oligosaccharide | Molecular weight | Peak area | Weight percentage (%) |
|---|---|---|---|---|
| 1 | ΔIS | 665 | 331.50 | 61.03 |
| 2 | ΔIIIS | 563 | 41.30 | 6.44 |
| 3 | ΔIIS | 563 | 59.00 | 9.20 |
| 4 | ΔIA | 605 | 9.90 | 1.65 |
| 5 | ΔIVS | 461 | 25.30 | 3.23 |
| 6 | ΔIIIA | 503 | 18.00 | 2.51 |
| 7 | ΔIIA | 503 | 26.70 | 3.72 |
| 8 | ΔIVA | 401 | 32.56 | 3.61 |
| 9 | ΔIIS$_{gal}$ | 563 | 4.50 | 0.70 |
| 11 | ΔIIA-IISglu | 1168 | 9.00 | 2.91 |
| 12 | ΔIIA-IVSglu | 1066 | 2.50 | 0.74 |
| 13 | Trisaccharide | 965 | 4.00 | 1.07 |
| 14 | 1,6-AnhydroΔIS-IS | 1210 | 4.80 | 1.61 |
| 15 | 1,6-Anhydro ΔIS | 545 | 6.30 | 0.95 |
| 16 + 17 | 1,6-Anhydro ΔIIS | 443 | 5.20 | 0.64 |

The weight percentage of trace disaccharide ΔIVS$_{gal}$ (peak 10) cannot be accurately quantified, and can be neglected due to its extremely low abundance.

Example 4

Sample Analysis 2

Separations by CE were performed on Beckman MDQ CE system. The fused silica capillary had an inner diameter of 50 μm and a total length of 80 cm; the running buffer included 200 mM Tris-H$_3$PO$_4$ and 2 mM MgCl$_2$, at pH 2.7; 1.3% (m/v) of polyethylene glycol having a molecular weight of 10000 should be added to the buffer solution immediately before use; the injection pressure was 55 mbar, and the injection time was 10 s; the separation voltage was −22 kV; after the monosulfated disaccharide ΔIIA was eluted, a pressure of 138 mbar was applied to push ΔIVA to the detection window for detection; the column temperature was 25° C.; and the UV detection wavelength was 230 nm.

Figure 4:
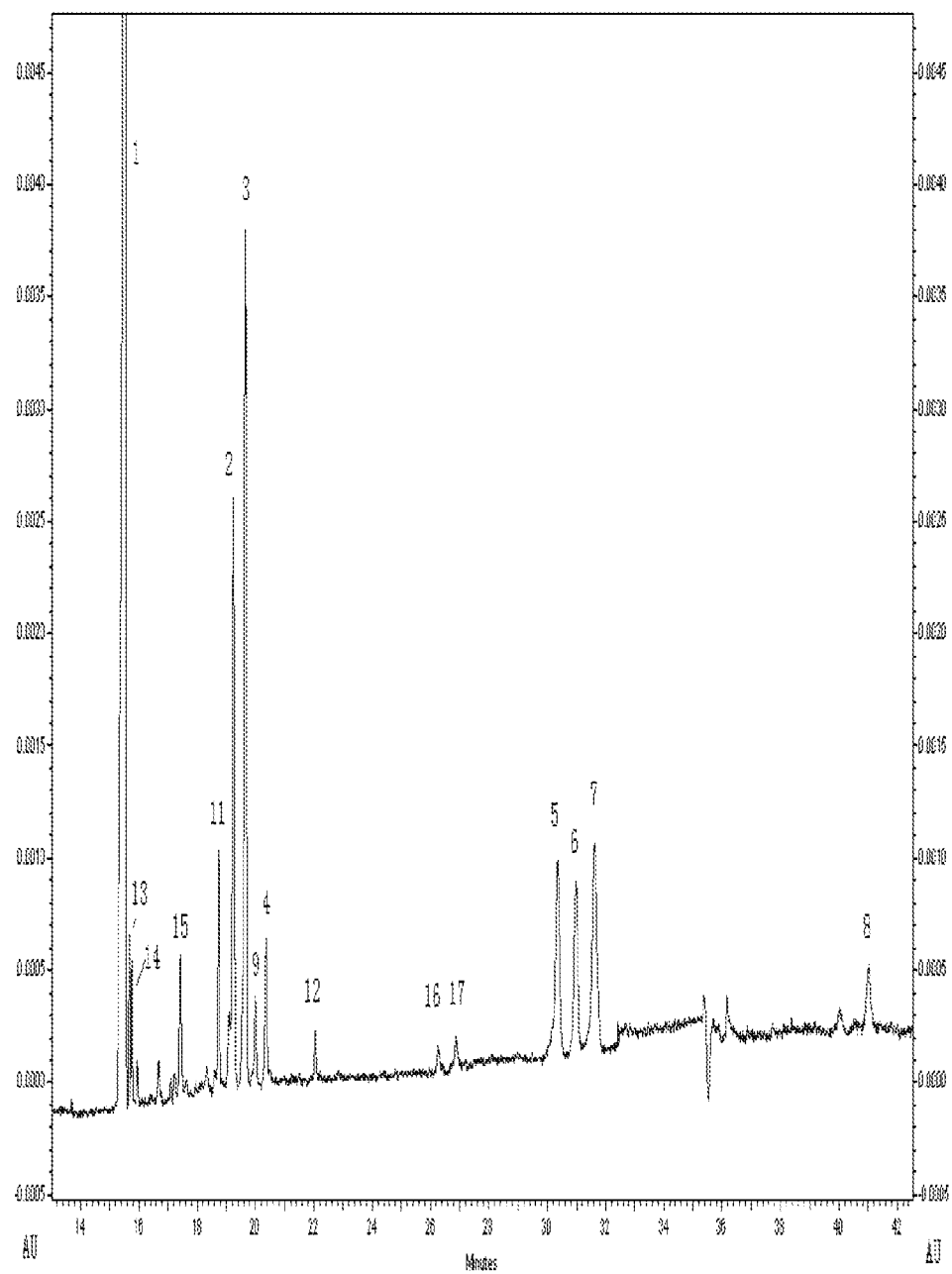
FIG. 4 is a electropherogram of exhaustively digested samples of enoxaparin sodium (USP reference standard), and the experiments are performed on the BECKMAN MDQ CE system.

The electropherogram of exhaustively digested enoxaparin sodium with capillary electrophoresis was shown in FIG. 4. The determined peak areas and the weight percentage of each oligosaccharide obtained from exhaustively digested enoxaparin sodium were listed in Table 3.

TABLE 3

The weight percentage of individual oligosaccharide obtained from exhaustively digested enoxaparin sodium.

| Peak number | Oligosaccharide | Molecular weight | Peak area | Weight percentage (%) |
|---|---|---|---|---|
| 1 | ΔIS | 665 | 5795.12 | 66.94 |
| 2 | ΔIIIS | 563 | 643.21 | 6.294 |
| 3 | ΔIIS | 563 | 900.13 | 8.804 |
| 4 | ΔIA | 605 | 147.85 | 1.554 |
| 5 | ΔIVS | 461 | 248.91 | 1.994 |
| 6 | ΔIIIA | 503 | 186.49 | 1.63 |
| 7 | ΔIIA | 503 | 271.85 | 2.38 |
| 8 | ΔIVA | 401 | 49.84 | 0.35 |
| 9 | ΔIIS$_{gal}$ | 563 | 77 | 0.75 |
| 11 | ΔIIA-IISglu | 1168 | 172.54 | 3.50 |
| 12 | ΔIIA-IVSglu | 1066 | 33.43 | 0.62 |
| 13 | Trisaccharide | 965 | 105.38 | 1.77 |
| 14 | 1,6-AnhydroΔIS-IS | 1210 | 85.53 | 1.80 |
| 15 | 1,6-Anhydro ΔIS | 545 | 132.95 | 1.26 |
| 16 + 17 | 1,6-Anhydro ΔIIS | 443 | 48.84 | 0.38 |

The weight percentage of trace disaccharide ΔIVS$_{gal}$ (peak 10) cannot be accurately quantified, and can be neglected due to its extremely low abundance.

According to the formula $$W_n\% = 100 \times \frac{Mw_n \times Area_n}{\sum Mw_x \times Area_x},$$

or formulae (4), (5) and (6), the weight percentage of each oligosaccharide obtained from exhaustively digested enoxaparin sodium was calculated (as listed in table 3), in which 1,6-anhydro oligosaccharides 14, 15 and 16+17 accounted for 1.80%, 1.26% and 0.38%, respectively. It was known that the USP enoxaparin sodium tested in our experiment had a weight-average molecular weight of 4432, and the molar percentage of oligosaccharide chains with 1,6-anhydro ring in enoxaparin sodium was 20.58%, calculated by formula (7) or (8).

What is claimed is:

1. A capillary electrophoresis (CE) method for fine structural analysis of enoxaparin sodium, comprising:

(1) digesting an enoxaparin sodium sample exhaustively with a mixture of heparin degrading enzymes;

(2) separating oligosaccharides in the digested enoxaparin sodium sample by capillary electrophoresis, wherein the oligosaccharides include disaccharides, trisaccharides, tetrasaccharides and oligosaccharides with 1,6-anhydro structure, wherein the capillary electrophoresis is conducted under the following conditions;

(a) a fused silica capillary having a total length ranging from 50 to 100 cm and an inner diameter ranging from 25 to 75 μm;

(b) a running buffer including NaH$_2$PO$_4$—H$_3$PO$_4$, Tris-H$_3$PO$_4$ or LiH$_2$PO$_4$—H$_3$PO$_4$, or any combinations thereof, in a concentration ranging from 150 to 300 mM, and in a pH ranging from 1.5 to 4.0; the running buffer further comprises MgCl$_2$ or ZnCl$_2$ in a concentration ranging from 1 to 5 mM, and polyethylene glycol (PEG) having a molecular weight from 5000 to 100,000 Da in a concentration ranging from 0.1% to 5% (m/v);

(c) a separation voltage ranging from −15 to −30 kV;

(d) an injection pressure ranging from 1 to 100 mbar and the injection time ranges from 1 to 60 seconds;

(e) a capillary temperature ranging from 10 to 40° C.; and (f) a UV detection wavelength ranging from 230 to 235 nm; wherein:

after elution of sulfated disaccharide ΔIIA of the structure:

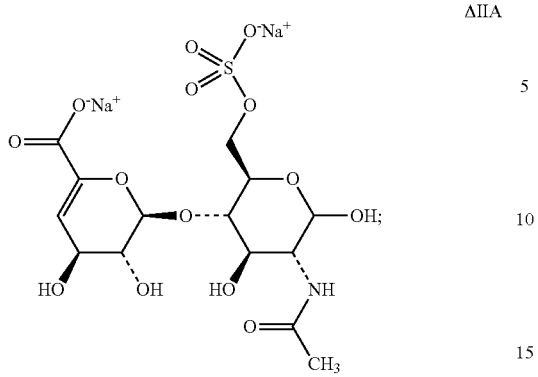
ΔIIA an alternative pressure ranging from 5 to 150 mbar is applied to push disaccharide ΔIVA of the structure:

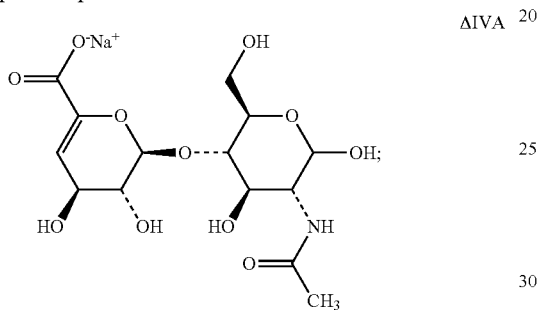
ΔIVA to a detection window for detection;
(3) after said elution step (2) pairing peaks present in an electropherogram from the capillary electrophoresis to the oligosaccharides in the digested enoxaparin sodium sample according to the linear relationship between electrophoretic mobilities and charge-to-mass ratio of the oligosaccharides; and
(4) quantitatively determining the percentage of each oligosaccharide in total oligosaccharides in the digested enoxaparin sodium sample by using a measured normalized chromatographic peak area.

2. The method according to claim 1, wherein the heparinase mixture used in step (1) includes at least two of heparinase I, heparinase II, and heparinase III.

3. The method according to claim 2, wherein the heparinase mixture used in step (1), includes heparinase I, heparinase II and heparinase III at a ratio of 1:1:1.

4. The method according to claim 1, wherein any one of, or a combination of the following conditions are met:
(a) the oligosaccharides with 1,6-anhydro structure obtained from exhaustively digested enoxaparin sodium in step (2) include compounds having the structures of:

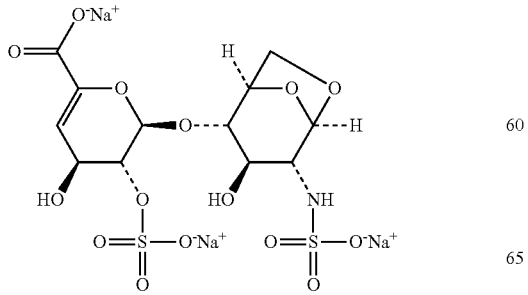

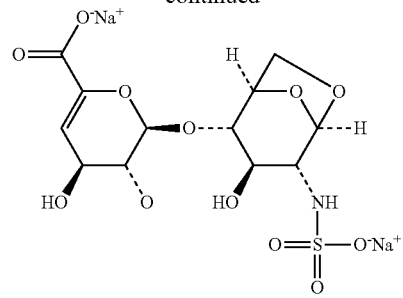

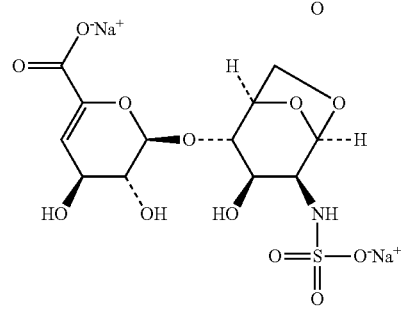

(b) the trisaccharide obtained from exhaustively digested enoxaparin sodium in step (2) include compounds having the structure of:

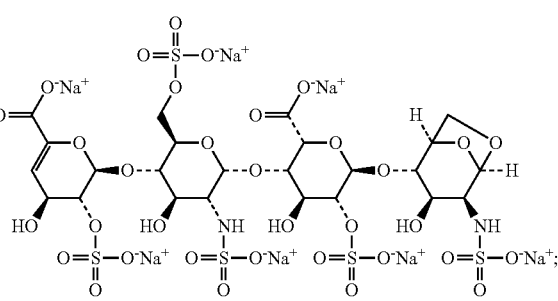

(c) the disaccharides obtained from exhaustively digested enoxaparin sodium in step (2) include compounds having the structures of:

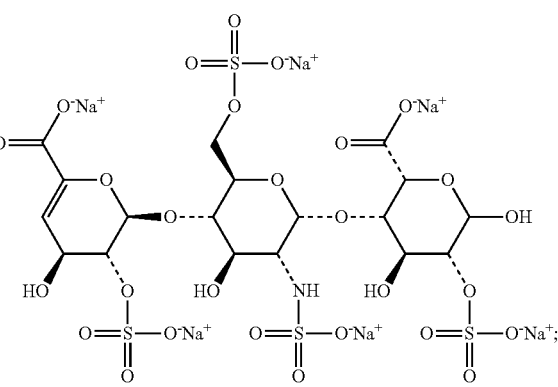

ΔIA
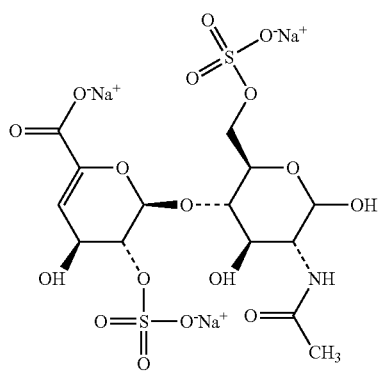
ΔIS
ΔIIA
ΔIIS
ΔIIIA
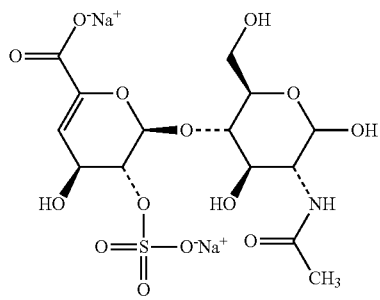
ΔIIIS
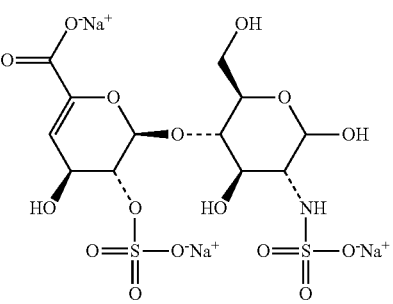
ΔIVA
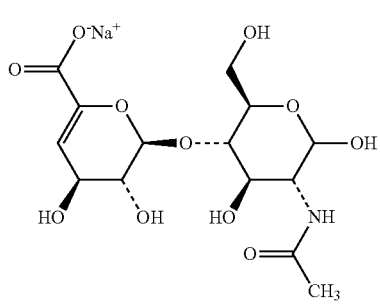
ΔIVS
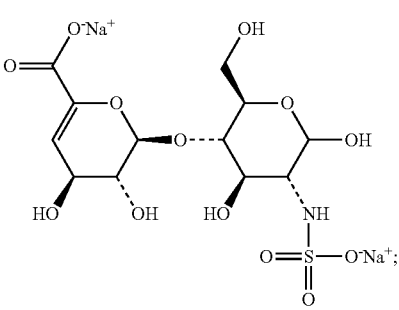
(d) two other disaccharides components, designated as $\Delta IIS_{gal}$ and $\Delta IVS_{gal}$ and obtained from exhaustively digested enoxaparin sodium sample in step (2), have the structures of:

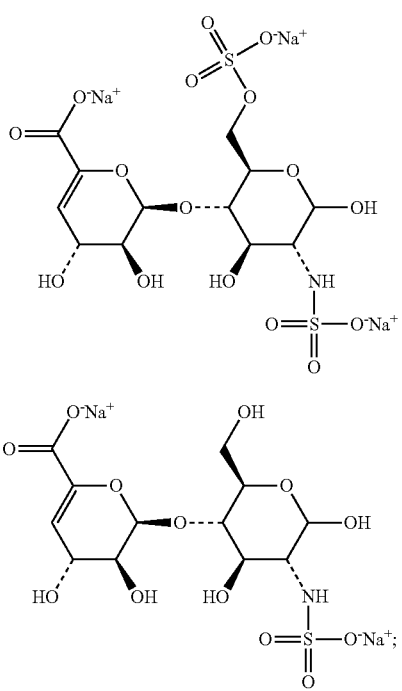

and
(e) two tetrasaccharides, designated as ΔIIA-IISglu and ΔIIa-IVSglu and obtained from the digested enoxaparin sodium sample in step (2), have the structures of:

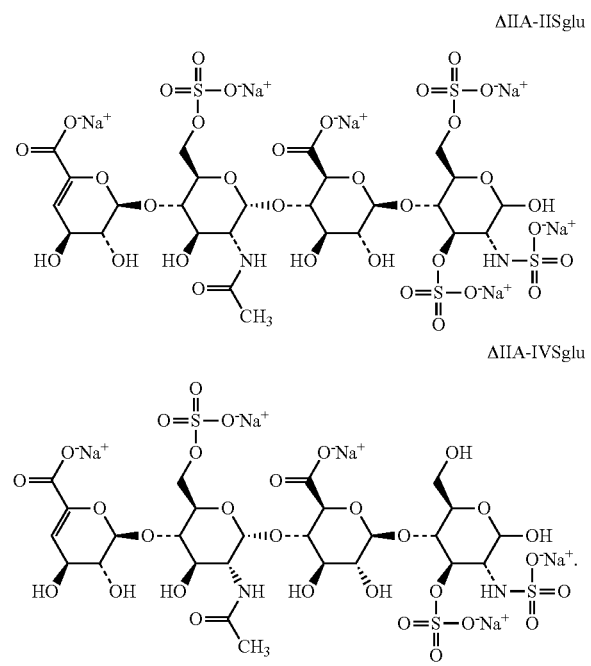

5. The method according to claim 1, wherein:
(a) the fused silica capillary has a total length ranging from 70 to 100 cm and an inner diameter ranging from 40 to 60 μm;
(b) the concentration of the running buffer ranges from 200 to 250 mM and the pH ranges from 2.0 to 4.0, the running buffer further comprises $MgCl_2$ or $ZnCl_2$ in a concentration ranging from 2 to 4 mM, and polyethylene glycol (PEG) having a molecular weight from 10000 to 50000 Da in a concentration ranging from 1% to 3% (m/v);
(c) the separation voltage ranges from −20 to −25 kV;
(d) the injection pressure ranges from 40 to 50 mbar and the injection time ranges from 10 to 20 seconds;
(e) the capillary temperature ranges from 20 to 30° C.; and
(f) the UV detection wavelength ranges from 230 to 232 nm.

6. The method according to claim 1, wherein the capillary electrophoresis of step (2) is conducted under the following conditions:
(a) the fused silica capillary has a total length ranging from 70 to 100 cm and an inner diameter ranging from 40 to 60 μm;
(b) the concentration of $NaH_2PO_4$—$H_3PO_4$, Tris-$H_3PO_4$ or $LiH_2PO_4$—$H_3PO_4$ in the running buffer ranges from 200 to 250 mM and the pH ranges from 2.0 to 4.0, the running buffer further comprising $MgCl_2$ or $ZnCl_2$ in a concentration ranging from 1-5 mM, and PEG having a molecular weight ranging from 5000 to 100,000 Da in a concentration ranging from 0.1%-5.0% (m/v);
(c) the separation voltage ranges from −20 to −25 kV;
(d) the injection pressure ranges from 40 to 50 mbar and the injection time ranges from 10 to 20 seconds;
(e) the capillary temperature ranges from 20 to 30° C.; and
(f) the UV detection wavelength ranges from 230 to 232 nm.

7. The method according to claim 1, wherein step (3) further comprises the following:
subjecting standard samples of at least 5 sulfated disaccharides to electrophoresis separation to determine their electrophoretic mobility;
constructing a correlation plot of electrophoretic mobility to the charge-to-mass ratio of the at least 5 sulfated disaccharides;
obtaining a linear equation describing the relationship between electrophoretic mobility μ and charge-to-mass ratio Z/M by linear regression analysis; and
predicting the electrophoretic mobility of other oligosaccharides according to the linear equation, which can be used to identify these oligosaccharides in the absence of reference standards.

8. The method according to claim 7, wherein the at least 5 sulfated disaccharides are selected from ΔIS, ΔIIIS, ΔIIS, ΔIA, ΔIIA, and ΔIIIA, having the following structures:

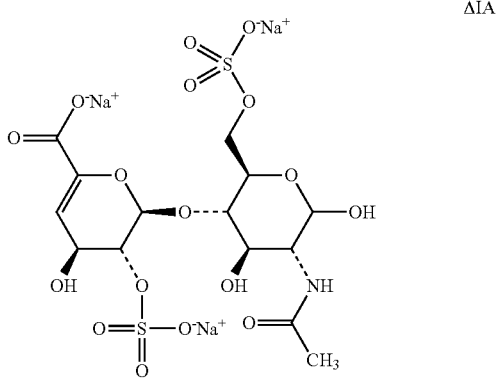

ΔIIA
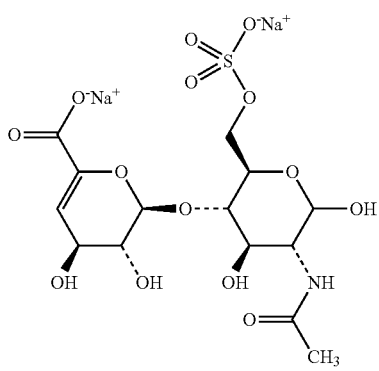

ΔIIIA
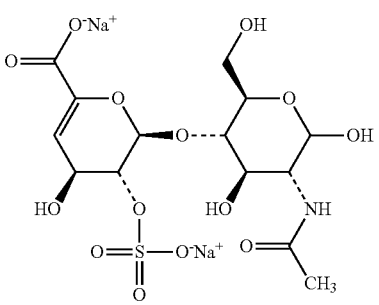

ΔIS
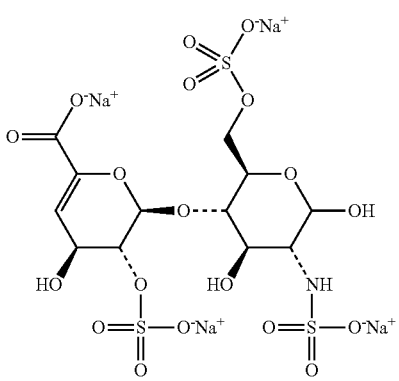

ΔIIS
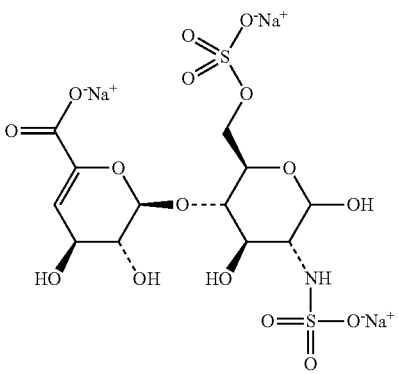

ΔIIIA
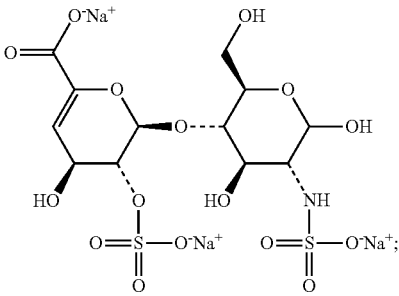

ΔIIIS and the step of obtaining a linear equation describing the relationship between electrophoretic mobility μ and charge-to-mass ratio Z/M by linear regression analysis uses the formula:

$$\frac{Z}{M} = 1.56\mu - 0.30$$

wherein Z/M is charge-to-mass ratios of an oligosaccharide; and μ is the electrophoretic mobility of the oligosaccharide.

9. The method according to claim 1, wherein the step of quantitatively determining the percentage of each oligosaccharide in total oligosaccharides in the digested enoxaparin sodium sample uses the formula:

$$W_n \% = 100 \times \frac{Mw_n \times Area_n}{\sum Mw_x \times Area_x}$$

wherein $Mw_n$ represents the molecular weight of any oligosaccharide; $Area_n$ represents the peak area of the oligosaccharide in the electropherogram; $Mw_x$ and $Area_x$ represent molecular weight and the peak area of a peak number.

10. A method for quantitatively determining the molar percentage of oligosaccharide chains with 1,6-anhydro structure in enoxaparin sodium, comprising the following steps:
(1) digesting an enoxaparin sodium sample exhaustively with a mixture of heparin degrading enzymes;
(2) separating oligosaccharides in the digested enoxaparin sodium sample by capillary electrophoresis, wherein the oligosaccharides include disaccharides, trisaccharides, tetrasaccharides and oligosaccharides with 1,6-anhydro structure, wherein the capillary electrophoresis is conducted under the following conditions;
(a) a fused silica capillary having a total length ranging from 50 to 100 cm and an inner diameter ranging from 25 to 75 μm;
(b) a running buffer including $NaH_2PO_4$—$H_3PO_4$, Tris-$H_3PO_4$ or $LiH_2PO_4$—$H_3PO_4$, or any combinations thereof, in a concentration ranging from 150 to 300 mM, and in a pH ranging from 1.5 to 4.0; the running buffer further comprises $MgCl_2$ or $ZnCl_2$ in a concentration ranging from 1 to 5 mM, and polyethylene glycol (PEG) having a molecular weight from 5000 to 100,000 Da in a concentration ranging from 0.1% to 5% (m/v);
(c) a separation voltage ranging from −15 to −30 kV;
(d) an injection pressure ranging from 1 to 100 mbar and the injection time ranges from 1 to 60 seconds;
(e) a capillary temperature ranging from 10 to 40° C.; and
(f) a UV detection wavelength ranging from 230 to 235 nm; wherein:

after elution of sulfated disaccharide ΔIIA of the structure:

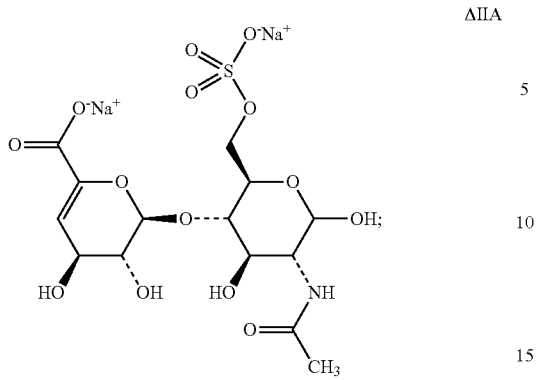

ΔIIA an alternative pressure ranging from 5 to 150 mbar is applied to push disaccharide ΔIVA of the structure:

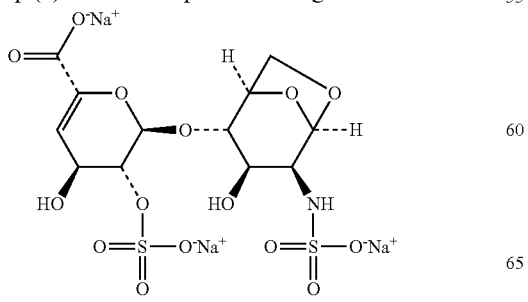

ΔIVA to a detection window for detection;

(3) after said elution step (2) pairing peaks present in an electropherogram from the capillary electrophoresis to the oligosaccharides in the digested enoxaparin sodium sample according to the linear relationship between electrophoretic mobilities and charge-to-mass ratio of the oligosaccharides and identifying the peaks of the oligosaccharide with 1,6-anhydro ring structure; and (4) quantitatively determining the amount of the oligosaccharides with 1,6-anhydro ring structure according to their peak areas, and further determining the molar percentage of the 1,6-anhydro ring structure in the enoxaparin sample.

11. The method according to claim 10, wherein the heparinase mixture comprises heparinase I, heparinase II and heparinase III.

12. The method according to claim 10, wherein any one of, or a combination of the following conditions are met:

(a) the oligosaccharides with 1,6-anhydro structure obtained from exhaustively digested enoxaparin sodium in step (2) include compounds having the structures of:

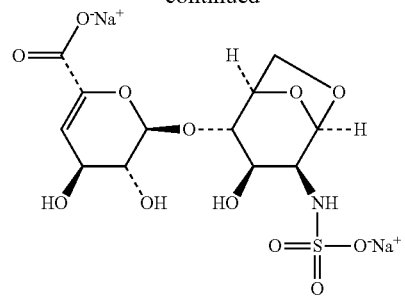

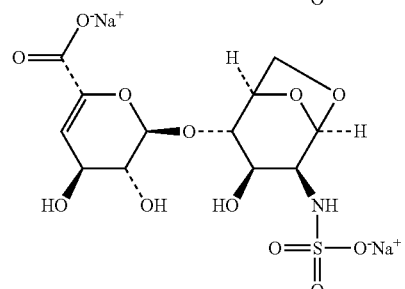

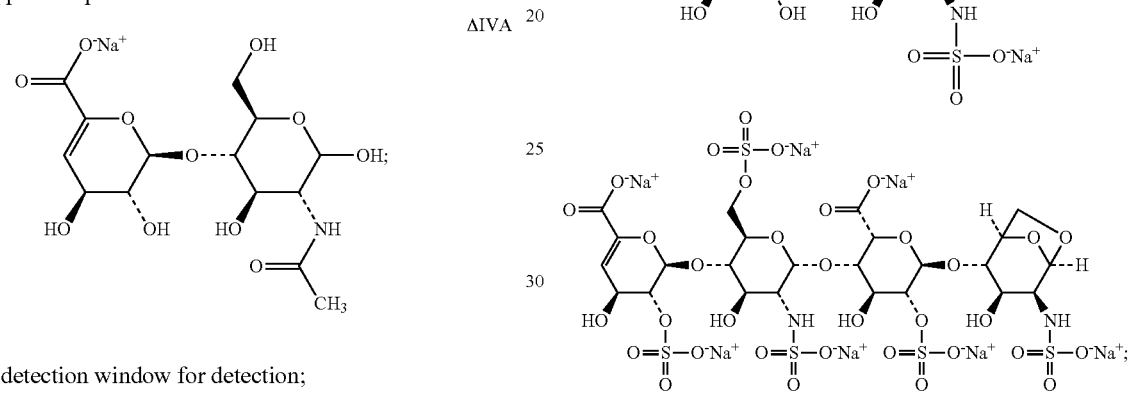

(b) the trisaccharide obtained from exhaustively digested enoxaparin sodium in step (2) include compounds having the structure of:

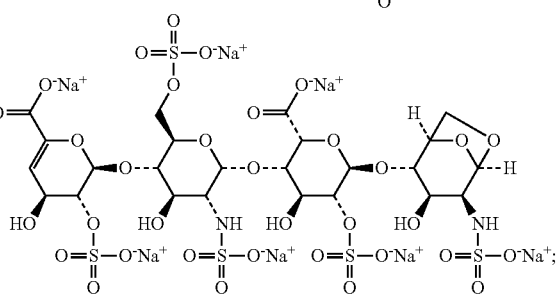

(c) the disaccharides obtained from exhaustively digested enoxaparin sodium in step (2) include compounds having the structures of:

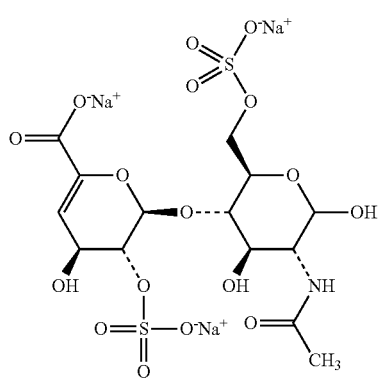
ΔIA
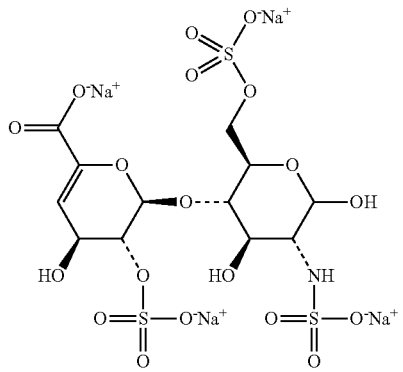
ΔIS
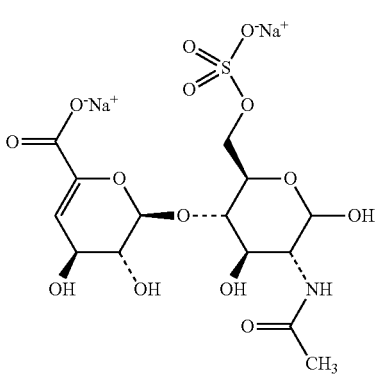
ΔIIA
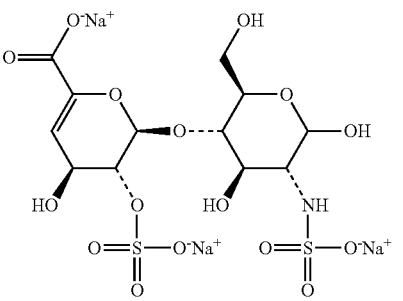
ΔIIS
ΔIIIA
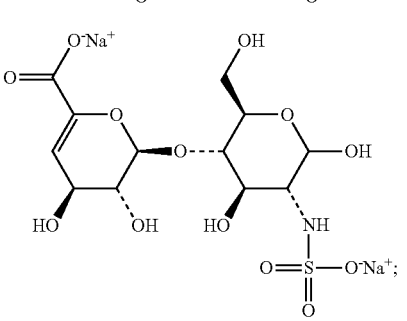
ΔIIIS
ΔIVS
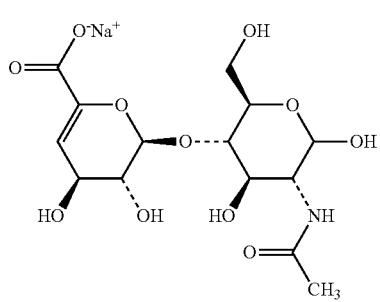
ΔIVA
(d) two other disaccharides components, designated as ΔIIS$_{gal}$ and ΔIVS$_{gal}$ and obtained from exhaustively digested enoxaparin sodium sample in step (2), have the structures of:

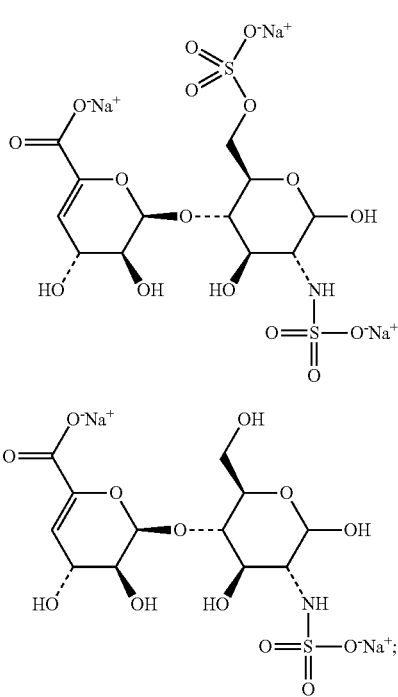

and (e) two tetrasaccharides, designated as ΔIIA-IISglu and ΔIIa-IVSglu and obtained from the digested enoxaparin sodium sample in step (2), have the structures of:

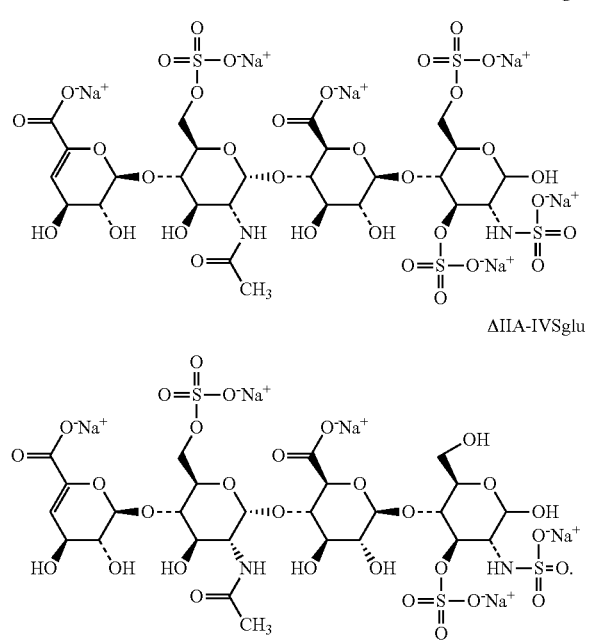

13. The method according to claim 10, wherein the capillary electrophresis of step (2) is conducted under the following conditions:

(a) the fused silica capillary has a total length ranging from 70 to 100 cm and an inner diameter ranging from 40 to 60 μm;

(b) the concentration of $NaH_2PO_4$—$H_3PO_4$, Tris-$H_3PO_4$ or $LiH_2PO_4$—$H_3PO_4$ in the running buffer ranges from 200 to 250 mM and the pH ranges from 2.0 to 4.0, the running buffer further comprising $MgCl_2$ or $ZnCl_2$ in a concentration ranging from 1-5 mM, and PEG having a molecular weight ranging from 5000 to 100,000 Da in a concentration ranging from 0.1%-5.0% (m/v);

(c) the separation voltage ranges from −20 to −25 kV;

(d) the injection pressure ranges from 40 to 50 mbar and the injection time ranges from 10 to 20 seconds;

(e) the capillary temperature ranges from 20 to 30° C.; and (f) the UV detection wavelength ranges from 230 to 232 nm.

14. The method according to claim 10, wherein the capillary electrophresis of step (2) is conducted under the following conditions:

(a) the fused silica capillary has a total length ranging from 70 to 100 cm and an inner diameter ranging from 40 to 60 μm;

(b) the concentration of $NaH_2PO_4$—$H_3PO_4$, Tris-$H_3PO_4$ or $LiH_2PO_4$—$H_3PO_4$ in the running buffer ranges from 200 to 250 mM and the pH ranges from 2.0 to 4.0, the running buffer further comprising $MgCl_2$ or $ZnCl_2$ in a concentration ranging from 1-5 mM, and PEG having a molecular weight ranging from 5000 to 100,000 Da in a concentration ranging from 0.1%-5.0% (m/v);

(c) the separation voltage ranges from −20 to −25 kV;

(d) the injection pressure ranges from 40 to 50 mbar and the injection time ranges from 10 to 20 seconds;

(e) the capillary temperature ranges from 20 to 30° C.; and (f) the UV detection wavelength ranges from 230 to 232 nm.

15. The method according to claim 10, wherein step (3) further comprises the following:

subjecting standard samples of at least 5 sulfated disaccharides to electrophoresis separation to determine their electrophoretic mobility;

constructing a correlation plot of electrophoretic mobility to the charge-to-mass ratio of the at least 5 sulfated disaccharides;

obtaining a linear equation describing the relationship between electrophoretic mobility μ and charge-to-mass ratio Z/M by linear regression analysis; and predicting the electrophoretic mobility of other oligosaccharides with 1,6-anhydroring structure according to the linear equation, which can be used to identify these oligosaccharides in the absence of reference standards.

16. The method according to claim 15, wherein the at least 5 sulfated disaccharides are selected from ΔIS, ΔIIIS, ΔIIS, ΔIA, ΔIIA, and ΔIIIA, having the following structures:

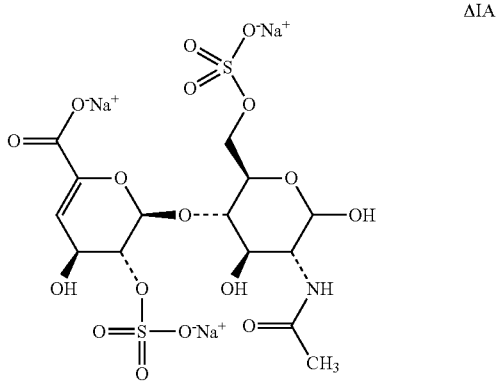

and the step of obtaining a linear equation describing the relationship between electrophoretic mobility μ and charge-to-mass ratio Z/M by linear regression analysis uses the formula:

$$\frac{Z}{M} = 1.56\mu - 0.30$$

wherein Z/M is charge-to-mass ratios of an oligosaccharide; and μ is the electrophoretic mobility of the oligosaccharide.

17. The method according to claim 10, wherein steps (3) and (4) comprise the following:

subjecting standard samples of at least 5 sulfated disaccharides selected from the group consisting of ΔIS, ΔIIIS, ΔIIS, ΔIA, ΔIIA, and ΔIIIA to electrophoresis separation to determine their electrophoretic mobility;

constructing a correlation plot of electrophoretic mobility to the charge-to-mass ratio of the at least 5 sulfated disaccharides;

obtaining a linear equation describing the relationship between electrophoretic mobility μ and charge-to-mass ratio Z/M by linear regression analysis using the formula:

$$\frac{Z}{M} = 1.56\mu - 0.30,$$

where Z/M is charge-mass ratio of an oligosaccharide, and μ is electrophoretic mobility of the oligosaccharide;

predicting the electrophoretic mobility of other oligosaccharides according to the linear equation to identify these oligosaccharides in the absence of standard samples;

calculating the weight percentage in the exhaustively digested enoxaparin sodium by the formulae:

$$w_{16+17}\ \% = 100 \times \frac{433(Area_{16} + Area_{17})}{\sum (Mw_x \times Area_x)}$$

$$w_{14}\ \% = 100 \times \frac{545 \times Area_{14}}{\sum (Mw_x \times Area_x)}$$

$$w_{15}\ \% = 100 \times \frac{1210 \times Area_{15}}{\sum (Mw_x \times Area_x)}$$

where $M_{W_x}$ and $Area_x$ represent molecular weight and the peak area of each oligosaccharide obtained from exhaustively digested enoxaparin sodium respectively;

determining the areas of peaks corresponding to disaccharide 1 (1,6-Anhydro ΔIIS), disaccharide 2 (1,6-Anhydro ΔIIS), disaccharide 3 (1,6-Anhydro ΔIS), and tetrasaccharide 1 (1,6-Anhydro ΔIS-IS); and calculating the molar percentage of oligosaccharides with 1,6-anhydro ring structure in the enoxaparin sodium by the formulae:

$$1,6 Anhydro\ \% = W_x \times \left(\frac{w_{16+17}\ \%}{443} + \frac{w_{14}\ \%}{545} + \frac{w_{15}\ \%}{1210}\right)$$

$$1,6 Anhydro\ \% = 100 \times W_x \times \frac{(Area_{14} + Area_{15} + Area_{16} + Area_{17})}{\sum (Mw_x \times Area_x)}$$

where $W_x$ represents weight-average molecular weight of enoxaparin sodium;

and further wherein:

ΔIS, ΔIIIS, ΔIIS, ΔIA, ΔIIA, and ΔIIIA have the following structures:

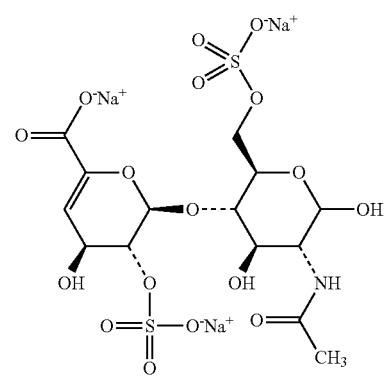
ΔIA

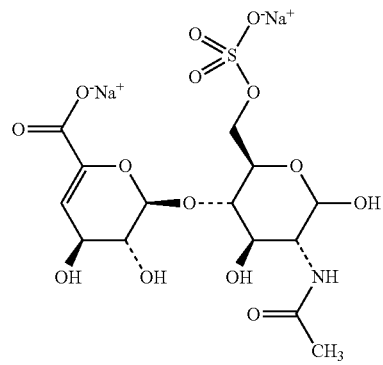
ΔIIA

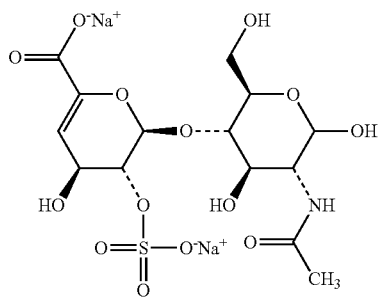
ΔIIIA

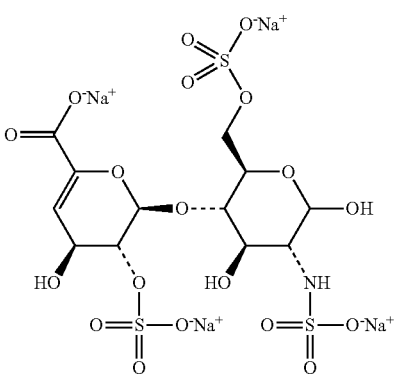
ΔIS

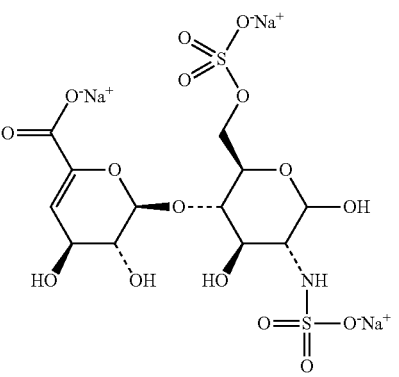
ΔIIS

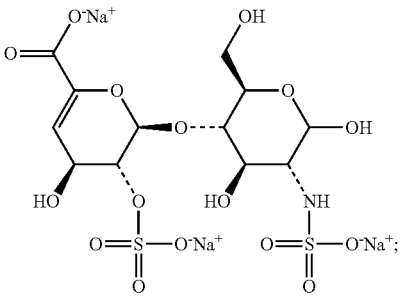
ΔIIIS peaks 16, 17, 15, and 14 of an electropherogram from the capillary electrophoresis correspond to disaccharide 1 (1,6-Anhydro ΔIIS), disaccharide 2 (1,6-Anhydro ΔIIS), disaccharide 3 (1,6-Anhydro ΔIS), and tetrasaccharide 1 (1,6-Anhydro ΔIS-IS);

and oligosaccharides with 1,6-anhydro structure includes disaccharide 1 (1,6-Anhydro ΔIIS), disaccharide 2 (1,6-Anhydro ΔIIS), disaccharide 3 (1,6-Anhydro ΔIS), and tetrasaccharide 1 (1,6-Anhydro ΔIS-IS).

* * * * *